US008273032B2

United States Patent
Carney et al.

(10) Patent No.: US 8,273,032 B2
(45) Date of Patent: Sep. 25, 2012

(54) PHYSIOLOGICAL PARAMETER MONITORING WITH MINIMIZATION OF MOTION ARTIFACTS

(75) Inventors: James Kevin Carney, Brooklyn Park, MN (US); Can Cinbis, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1088 days.

(21) Appl. No.: 12/182,847

(22) Filed: Jul. 30, 2008

(65) Prior Publication Data

US 2010/0030088 A1 Feb. 4, 2010

(51) Int. Cl.
*A61B 5/02* (2006.01)
(52) U.S. Cl. .................. 600/500; 600/502; 600/504
(58) Field of Classification Search .................. None
See application file for complete search history.

(56) References Cited

U.S. PATENT DOCUMENTS

| | | | |
|---|---|---|---|
| 4,425,920 A | 1/1984 | Bourland et al. | |
| 4,911,167 A | 3/1990 | Corenman et al. | |
| 4,934,372 A | 6/1990 | Corenman et al. | |
| 5,431,170 A | 7/1995 | Mathews | |
| 5,556,421 A | 9/1996 | Prutchi et al. | |
| 5,632,272 A | 5/1997 | Diab et al. | |
| 5,795,300 A | 8/1998 | Bryars | |
| 6,077,227 A * | 6/2000 | Miesel et al. | 600/486 |
| 6,331,162 B1 | 12/2001 | Mitchell | |
| 6,491,647 B1 | 12/2002 | Bridger et al. | |
| 7,072,702 B2 | 7/2006 | Edgar, Jr. et al. | |
| 2003/0036685 A1 | 2/2003 | Goodman | |
| 2004/0034293 A1 | 2/2004 | Kimball | |
| 2004/0111014 A1 * | 6/2004 | Hickle | 600/300 |
| 2006/0080047 A1 * | 4/2006 | Diab | 702/32 |
| 2006/0149144 A1 | 7/2006 | Lynn et al. | |
| 2007/0073124 A1 * | 3/2007 | Li et al. | 600/323 |
| 2007/0255330 A1 | 11/2007 | Lee et al. | |
| 2008/0208020 A1 | 8/2008 | Cinbis et al. | |

FOREIGN PATENT DOCUMENTS

WO 2004091719 A2 10/2004

OTHER PUBLICATIONS

Visram et al. Use of two oximeters to investigate a method of movement artefact rejection using photoplethysmographic signals. British Journal of Anaesthesia 72:388-392 (1994).*
DeMeulenaere, S. Pulse Oximetry: Uses and Limitations. The Journal for Nurse Practitioners, May 2007, pp. 312-317.*

(Continued)

*Primary Examiner* — Samuel Woolwine
(74) *Attorney, Agent, or Firm* — Michael J. Ostrom; Evans M. Mburu

(57) ABSTRACT

An implanted system includes at least two optical sensors implanted proximate to an artery of a patient such that one optical sensor is upstream of another optical sensor. Arterial pulses of the patient may be detected based on electrical signals from at least one of the optical sensors. In addition, electrical signals from the optical sensors may be used to minimize the effects of motion artifacts on the detection of arterial pulses. For example, a detected pulse may be determined to be a spurious pulse if the optical sensors indicate the occurrence of the pulse within a predetermined range of time. As another example, a first optical sensor signal may be shifted in time relative to a second optical sensor signal, and the signals may be correlated. An arterial pulse may be detected at a time at which a peak or trough amplitude value of the correlated signal is observed.

43 Claims, 9 Drawing Sheets

OTHER PUBLICATIONS (PCT/US2009/050788) PCT Notification of Transmittal of the International Search Report and the Written Opinion of the International Searching Authority, 11 pages.

Response to Rule 161(1) EPC communication from counterpart European Patent Application No. 09790507.9 dated Dec. 1, 2011 (7 pages).

* cited by examiner

PHYSIOLOGICAL PARAMETER MONITORING WITH MINIMIZATION OF MOTION ARTIFACTS

TECHNICAL FIELD

The disclosure relates to medical devices and, more particularly, to medical devices that monitor one or more physiological parameters of a patient.

BACKGROUND

Some medical devices may monitor one or more hemodynamic characteristics of a patient, such as the blood oxygen saturation level in arterial blood, arterial pulses of the patient, and the like. Example medical devices that monitor hemodynamic characteristics of a patient include optical sensors, such as pulse oximeters. One type of optical sensor includes at least one light source that emits light through a portion of blood-perfused tissue of a patient, and a detector that senses the emitted light that passed through the blood-perfused tissue. An intensity of the light sensed by the detector may be indicative of hemodynamic function of the patient, such as oxygen saturation of blood of the patient.

In some types of optical sensors, one or more light sources may be positioned on the same side of the blood perfused tissue as the detector, such that the detector detects light emitted by the light sources and reflected by blood. This type of optical perfusion sensor may be referred to as a reflectance optical sensor. In other types of optical sensors, referred to as transmissive sensors, one or more light sources may generally oppose the detector, such that the detector senses light that is transmitted through the blood perfused tissue.

SUMMARY

In general, the disclosure is directed toward reducing the effects of motion artifacts on a system including an optical sensor that monitors one or more physiological parameters of a patient. In some examples, an implantable medical system includes at least two optical sensors that may be implanted proximate to an artery of a patient, such that one optical sensor is downstream of the other optical sensor relative to a direction of blood flow through the artery. Arterial pulses of the patient may be detected based on electrical signals from at least one of the optical sensors. In addition, electrical signals from the optical sensors may be used to minimize the effects of motion artifacts on the detection of arterial pulses. A motion artifact may cause the optical sensors to generate electrical signals similar to that caused by an arterial pulse. In other examples, the optical sensors may be implanted proximate to different arteries of the patient.

A first optical sensor that is upstream of a second optical sensor relative to a direction of blood flow through an artery by which the optical sensors are implanted may detect an arterial pulse prior to the second optical sensor. Thus, the second optical sensor may generate an electrical signal indicative of a true arterial pulse after the first optical sensor generates an electrical signal indicative of the true arterial pulse. On the other hand, an electrical signal indicative of a motion artifact may be generated by the first and second optical sensors substantially simultaneously or within a predetermined range of time. Accordingly, in some examples, a detected pulse may be determined to be a spurious pulse if the optical sensors indicate the occurrence of the pulse within a predetermined range of time.

In other examples, an arterial pulse may be detected based on signals from both first and second optical sensors in order to help minimize the effects of motion artifacts on the detection of the arterial pulses. For example, a first optical sensor signal may be shifted in time relative to a second optical sensor signal, and the signals may be correlated. An arterial pulse may be detected at a time at which a peak or trough amplitude value of the correlated signal is observed.

In one aspect, the disclosure is directed to a method comprising receiving a first electrical signal from a first optical sensor implanted within a patient, receiving a second electrical signal from a second optical sensor implanted within the patient, detecting an arterial pulse of the patient based on at least one of the first or second electrical signals, and determining whether the arterial pulse is a spurious pulse based on the first and second electrical signals.

In another aspect, the disclosure is directed to an implantable medical system comprising a first optical sensor that generates a first electrical signal, a second optical sensor that generates a second electrical signal, and a processor that receives the first electrical signal and the second electrical signal, detects an arterial pulse of the patient based on at least one of the first or second electrical signals, and determines whether the arterial pulse is a spurious pulse based on the first and second electrical signals.

In another aspect, the disclosure is directed to an implantable medical system comprising means for receiving a first electrical signal from a first optical sensor implanted within a patient, means for receiving a second electrical signal from a second optical sensor implanted within the patient, means for detecting an arterial pulse of the patient based on at least one of the first or second electrical signals, and means for determining whether the arterial pulse is a spurious pulse based on the first and second electrical signals.

In another aspect, the disclosure is directed to a method comprising receiving a first electrical signal from a first optical sensor implanted within a patient, receiving a second electrical signal from a second optical sensor implanted within the patient, where the first and second optical sensors are positioned relative to each other such that the first optical sensor detects an arterial pulse of the patient before the second optical sensor, detecting a first signal characteristic of the first signal, detecting a second signal characteristic of the second signal, determining whether the first and second signal characteristics occurred within a predetermined range of time, and if the first and signal characteristics occurred within the predetermined range of time, determining that the first and second signal characteristics are artifacts.

In another aspect, the disclosure is directed to a method comprising receiving a first electrical signal from a first optical sensor implanted within a patient, receiving a second electrical signal from a second optical sensor implanted within the patient, shifting the first electrical signal in time relative to the second electrical signal to generate a time-shifted electrical signal, correlating the second electrical signal and the time-shifted electrical signal to generate a correlated signal, and detecting an arterial pulse of the patient based on the correlated signal. In some examples, detecting the arterial pulse comprises identifying a peak amplitude or a trough amplitude of the correlated signal, where the peak or the trough amplitude is associated with the arterial pulse of the patient. In addition, in some examples, shifting the first electrical signal in time relative to the second electrical signal to generate the time-shifted electrical signal comprises shifting the first electrical signal by 0.5 milliseconds to about 80 milliseconds.

In another aspect, the disclosure is directed to an implantable medical system comprising a first optical sensor that generates a first electrical signal, a second optical sensor that generates a second electrical signal, and a processor that receives the first electrical signal and the second electrical signal, shifts the first electrical signal in time relative to the second electrical signal to generate a time-shifted electrical signal, correlates the second electrical signal and the time-shifted electrical signal to generate a correlated signal, and detects an arterial pulse of a patient based on the correlated signal. In some examples, the processor detects the arterial pulse by at least identifying a peak amplitude or a trough amplitude of the correlated signal, where the peak amplitude or the trough amplitude is associated with the arterial pulse of the patient. In addition, in some examples, the processor shifts the first electrical signal in time relative to the second electrical signal to generate the time-shifted electrical signal by at least shifting the first electrical signal by about 0.5 milliseconds to about 80 milliseconds.

In another aspect, the disclosure is directed to an implantable medical system comprising means for receiving a first electrical signal from a first optical sensor implanted within a patient, means for receiving a second electrical signal from a second optical sensor implanted within the patient, means for shifting the first electrical signal in time relative to the second electrical signal to generate a time-shifted electrical signal, means for correlating the second electrical signal and the time-shifted electrical signal to generate a correlated signal, and means for detecting an arterial pulse of the patient based on the correlated signal.

In another aspect, the disclosure is directed to a computer-readable medium comprising instructions. The instructions cause a programmable processor to perform any one or more of the techniques described herein.

The details of one or more examples of the disclosure are set forth in the accompanying drawings and the description below. Other features, objects, and advantages will be apparent from the description and drawings, and from the claims.

DETAILED DESCRIPTION

Figure 1:
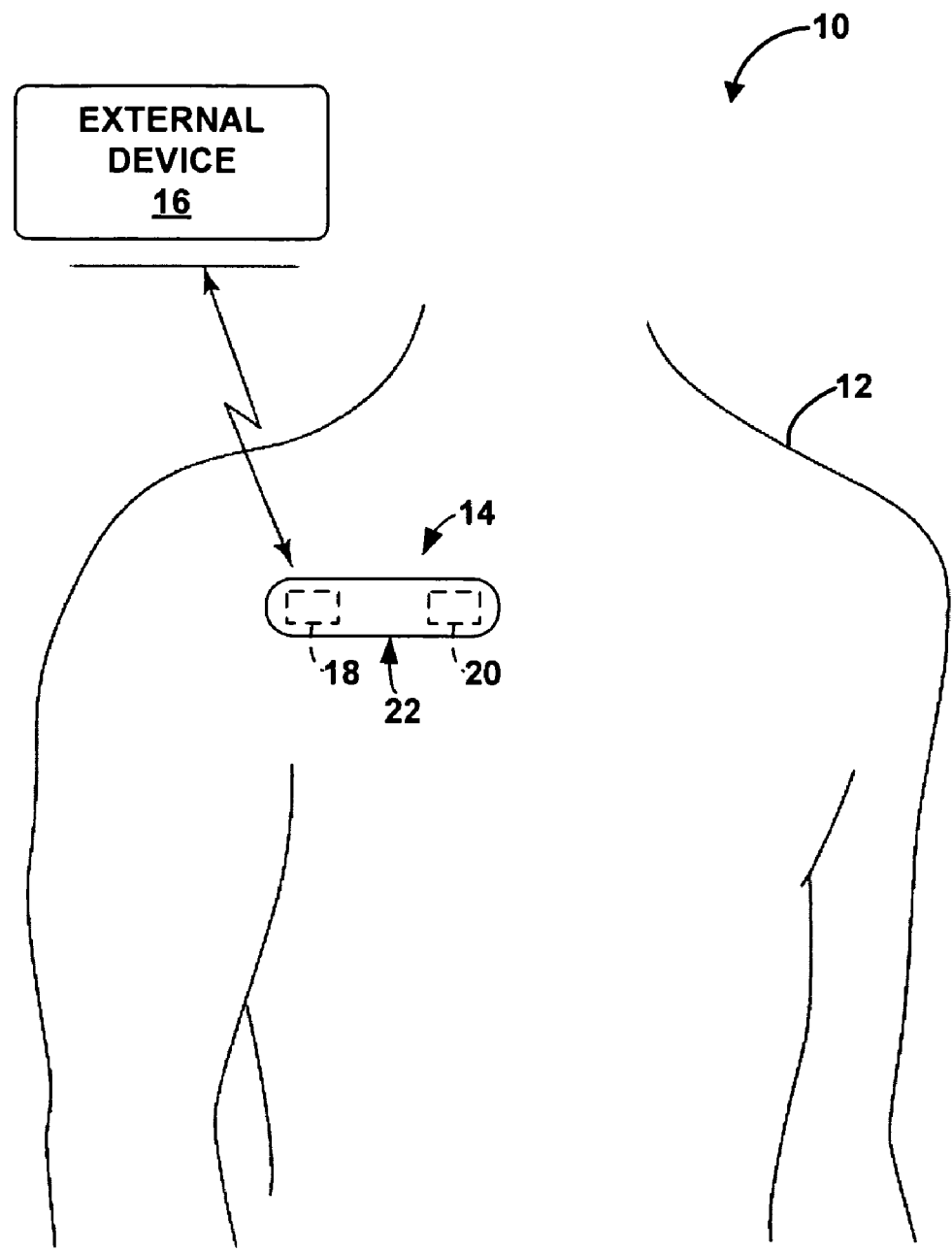
FIG. 1 is a conceptual diagram illustrating an example system that includes an implantable medical device (IMD) including an implantable optical sensor.

FIG. 1 is a conceptual diagram illustrating an example system 10 that may be used to monitor one or more physiological parameters of patient 12, such as a heart rhythm of patient 12 or an oxygen saturation level of blood of patient 12. Patient 12 ordinarily, but not necessarily, will be a human. Monitoring system 10 includes implantable medical device (IMD) 14 and external device 16. IMD 14 may be, for example, an implantable monitor that does not provide therapy (e.g., stimulation therapy) to patient 12. In other examples, IMD 14 may be configured to deliver stimulation to the heart of patient 12 or to deliver another type of therapy to patient 12 (e.g., delivery of a therapeutic agent). Neither IMD 14, external device 16 nor any of the figures drawn to any particular scale.

In the example shown in FIG. 1, IMD 14 is implanted within a subcutaneous tissue layer of patient 12. Due to its relatively small size, a clinician may implant IMD 14 through a relatively small incision in the patient's skin, or percutaneously, e.g., via an introducer. In other examples, IMD 14 may be implanted within other tissue sites, such as a submuscular location. IMD 14 may be a temporary diagnostic tool employed to monitor one or more physiological parameters of patient 12 for a relatively short period of time (e.g., days or weeks), or may be used on a more permanent basis, such as to control therapy delivery to patient 12. In some examples of the latter use of IMD 14, a separate therapy delivery device, such as a fluid delivery device, pacemaker, cardioverter or defibrillator, may be implanted within patient 12. The therapy delivery device may communicate with IMD 14 via a wired connection or via wireless communication techniques. In other examples, as previously described, IMD 14 may be incorporated in a common housing with a therapy delivery device.

IMD 14 includes first optical sensor 18 and second optical sensor 20, which is separated from first optical sensor 18 by a predetermined distance in some examples. Optical sensors 18, 20 are implanted within patient 12 proximate to vasculature of patient 12 (e.g., an artery). Optical sensors 18, 20 each generate an electrical signal that changes as a function of the amount of blood in tissue proximate to IMD 14, such as the amount of blood within an artery. Optical sensors 18, 20 may sense the changes in volume in an artery associated with contractions of the heart of patient. In this way, the electrical signal generated by at least one of the optical sensors 18, 20 may be used to detect arterial pulses of patient 12, which may be used to, for example, determine a heart rate of patient 12. In addition, in some examples, the electrical signal from at least one of the optical sensors 18, 20 may be used to determine a blood oxygen saturation level of patient.

In the example shown in FIG. 1, optical sensors 18, 20 each include at least one detector and at least one light source. The one or more light sources of each of the optical sensors 18, 20 may emit light at a particular wavelength, which is scattered through blood-perfused tissue, and the one or more detectors may each be configured to sense light that is emitted from the light source and transmitted through a medium, such as a blood mass (e.g., blood cells in an artery) of patient 12. In some examples, at least one of the optical sensors 18, 20 may include at least two light sources that emit light at different wavelengths and at least two detectors that are sensitive to different wavelengths of light.

In some examples, the arrangement between the detector and light source of each of the optical sensors 18, 20 described herein may define a reflectance type optical sensor because light that is emitted by the light source and reflected by blood in an artery or tissue of patient 12 is received by the detector. In contrast, an optical sensor including one or more detectors positioned to detect light emitted by one or more light sources and transmitted through blood in an artery or tissue of patient 12 may be referred to as a transmissive-type optical sensor. In this case, the detectors are oriented to receive light emitted by the light source and transmitted through tissue.

In the example shown in FIG. 1, the one or more light sources and detectors of each of the optical sensors 18, 20 are coupled to housing 22 of IMD 14. Housing 22 may be hermetically sealed and may enclose various sensing and control circuitry for sensing, storing and/or transmitting one or more physiological parameters of patient 12 to another device, and, in some cases, a therapy delivery module for delivering therapy to patient 12 (e.g., electrical stimulation or a therapeutic agent). In some examples, the one or more light sources and/or detectors of optical sensors 18, 20 extend from housing 22 or may be coupled to optically transmissive members that extend from housing 22 and guide light to a tissue site or collect light from a tissue site remote from housing 22. In other examples, the one or more light sources and/or optical detectors are separated from housing 22 and communicate with components within housing 22 via an electrical conductor (not shown) or a wireless communication link. Optical sensors 18, 20 that are separate from each other and movable relative to each other may be useful for, for example, customizing the distance between implanted optical sensors 18, 20.

The intensity of light detected by the detectors of optical sensors 18, 20 may be used to detect a pulsatile component (e.g., an arterial pulse associated with a heartbeat) of a cardiac cycle of patient 12. In particular, a change in volume in an artery or other vasculature of patient 12 may be detected based on one or more characteristics of the waveforms defined by the electrical signals generated by the detectors of optical sensors 18, 20. In this way, the signals generated by optical sensors 18, 20 may be used to generate a photoplethysmograph. The optical properties of blood-perfused tissue may change depending upon the relative amounts of oxygenated and deoxygenated hemoglobin due, at least in part, to their different optical absorption spectra. That is, the oxygen saturation level of the patient's blood may affect the amount of light that is absorbed by a blood mass and the amount of light that is reflected back to optical sensors 18, 20. Accordingly, an electrical signal generated by optical sensors 18, 20 that indicates the intensity of one or more wavelengths of light detected by the detector of the respective sensor 18, 20 may change based on the relative amounts of oxygenated and deoxygenated hemoglobin in the tissue, which may change following a heartbeat of patient 12.

As the heart of patient 12 contracts, blood is driven through the arteries of patient 12. The contraction of the heart may be referred to as systole. Oxygenated and deoxygenated hemoglobin within the blood may unequally absorb different wavelengths of light. Accordingly, the intensity of light that is emitted by the light sources of optical sensors 18, 20, transmitted through blood in an artery, and detected by the detector of the respective sensor 18, 20 may indicate the relative amount of blood in the blood mass monitored by optical sensors 18, 20. As blood flows from the heart of patient 12 through an artery following contraction of the heart, the amount of oxygenated hemoglobin in the blood in the artery may increase. Thus, maximum light absorbance by the blood may occur during systole, which may be indicated by a trough amplitude value, i.e., a nadir amplitude value, of the electrical signal waveform generated by optical sensors 18, 20. Maximum light absorbance by the blood may be associated with the occurrence of an arterial pulse.

Diastole may refer to the period of time when the heart relaxes after systole. During diastole, the intensity of light that is emitted by the light sources of optical sensors 18, 20 and transmitted through blood in an artery may increase compared to the intensity of light that is transmitted through blood during systole. In some cases, minimum light absorbance by the blood in an artery may occur during diastole, which may be indicated by a peak amplitude value in the waveform generated by the electrical signals from optical sensors 18, 20.

In some examples, an arterial pulse resulting from contraction of the heart of patient 12, which may indicate a heartbeat, may be characterized by a peak or trough amplitude value of an optical sensor signal. In other examples, the arterial pulse may be detected when an amplitude of the optical sensor signal falls below a threshold value, which may be determined by a clinician based on the optical sensor signals specific to patient 12 or more general to more than one patient. In addition, because the patient's blood oxygen levels may change, e.g., based on patient activity level, the threshold value may be a moving threshold value, and may be periodically updated.

In other examples, depending upon the wavelength of light emitted by optical sensors 18, 20, minimum light absorbance by the blood may occur during systole, which may be indicated by a peak amplitude of an optical sensor signal or an amplitude greater than a threshold value. Thus, in other examples, an arterial pulsation resulting from contraction of the heart of patient 12, may be characterized by an optical sensor signal amplitude that is greater than or equal to a particular threshold value. While a peak or trough amplitude value is primarily referred to throughout the description of FIGS. 2-7, in other examples, IMD 14 may detect an arterial pulse if the amplitude value of the optical sensor signal is less than or equal to a threshold value, or, in other examples, greater than or equal to a threshold value.

Mechanical vibration or other movement of optical sensors 18, 20, which may be attributable to movement of patient 12, may change the optical coupling between optical sensors 18, 20 and tissue of patient 12, e.g., due to temporary migration or displacement of the sensors, or compression or expansion of the tissue. This may result in a change in the relative position between the light sources and detectors of sensors 18, 20 and vasculature of patient 12, and may introduce motion artifacts into the electrical signals generated by optical sensors 18, 20. In examples in which optical sensors 18, 20 are implanted proximate to an artery to monitor the volume of blood in the artery, the movement of optical sensors 18, 20 may result in electrical signals that do not accurately and precisely indicate the volume of blood in the artery of patient. For example, due to movement between optical sensors 18, 20 and a blood mass, the detectors of optical sensors 18, 20 may generate signals indicating an arterial pulse when the heart of patient 12 is not actually contracting. That is, motion artifacts may cause optical sensors 18, 20 to generate signals indicating a spurious pulse.

As described in further detail below with reference to FIG. 3, optical sensors 18, 20 implanted within patient 12 a predetermined distance apart and proximate to an artery may be used to minimize the effects of motion artifacts on the detection of arterial pulses based on signals from optical sensors 18, 20. Because optical sensors 18, 20 are implanted proximate to an artery, one of the optical sensors 18 or 20 may be positioned closer to the heart of patient 12 than the other optical sensors 20 or 18, respectively. That is, one optical sensor may be positioned upstream of the other optical sensor relative to a blood flow through the artery, such that the upstream optical sensor detects an arterial pulse before the downstream optical sensor. Optical sensors 18, 20 may generate electrical signals that indicate a true arterial pulse, e.g., a signal that indicates maximum light absorbance by the blood in the artery, out of phase with each other. The propagation of blood through the artery proximate to IMD 14 may result in the phase difference between the peak or trough amplitude values of the electrical signal waveforms generated by optical sensors 18, 20 that indicate the true arterial pulse.

In contrast, artifacts resulting from movement of optical sensors 18, 20 relative to adjacent tissue may cause the optical sensors 18, 20 to generate electrical signals that indicate the occurrence of an arterial pulse substantially in phase, e.g., within a particular range of time. The artifact may be a signal characteristic that is associated with an arterial pulse, such as a trough amplitude of an electrical signal waveform. Thus, the detection of a pulse based on electrical signals from optical sensors 18, 20 within a predetermined range of time may indicate the detection of a spurious pulse, rather than a true arterial pulse. The motion artifact in the electrical signals generated by optical sensors 18, 20 may be ignored with the aid of common mode noise separation techniques, which are described in further detail below with reference to FIGS. 5 and 7.

In some examples, IMD 14 may also include electrodes that sense electrical activity of patient's heart. For example, IMD 14 may generate an electrogram (EGM) or electrocardiogram (ECG) based on signals from the electrodes. The electrical activity of the patient's heart may also be used to eliminate motion artifacts from the electrical signals generated by optical sensors 18, 20.

In some examples, IMD 14 may be implanted within patient 12 such that optical sensors 18, 20, or at least the detectors of optical sensors 18, 20, face away from the epidermis of patient 12 in order to help minimize interference from background light, e.g., from outside of the patient's body. Background light may include light from a source other than the one or more light sources of the respective optical sensor 18, 20. Detection of the background light by the detectors of optical sensors 18, 20 may result in an inaccurate and imprecise detection of an arterial pulse or of a blood oxygen saturation level of patient.

As described in further detail below with reference to FIG. 2, IMD 14 may include a memory that stores electrical signals generated by optical sensors 18, 20. In addition or alternatively, IMD 14 may transmit electrical signals or information derived from the electrical signals (e.g., a heart rhythm of patient 12) generated by optical sensors 18, 20 to another implanted or external device, such as external device 16. In some examples, a clinician may retrieve stored information from IMD 14 after explanting IMD 14 from patient 12. In other examples, the clinician (or other user) may interrogate IMD 14 with external device 16 while IMD 14 remains implanted within patient 12 in order to retrieve stored information from IMD 14.

IMD 14 may be useful for monitoring physiological parameters, such as the heart rate and blood oxygen saturation level, of patient 12. The monitored physiological parameter values may provide useful information for diagnosing a patient condition or formulating a treatment plan for patient 12. For example, if patient 12 experiences syncope, e.g., periodic fainting, IMD 14 may be used to determine the physiological parameters that are associated with the syncope. A clinician may review the associated physiological parameters to determine a potential cause of the syncopic events. For example, a clinician may determine whether any patient events occurred based on the recorded signals from optical sensors 18, 20. Such events may be confirmed by other types of sensors, such as accelerometers, blood pressure sensors, or the like.

External device 16 may be a handheld computing device or a computer workstation. External device 16 may include a user interface that receives input from a user, such as a clinician. The user interface may include, for example, a keypad and a display, which may for example, be a cathode ray tube (CRT) display, a liquid crystal display (LCD) or LED display. The keypad may take the form of an alphanumeric keypad or a reduced set of keys associated with particular functions. External device 16 can additionally or alternatively include a peripheral pointing device, such as a mouse, via which a user may interact with the user interface. In some examples, a display of external device 16 may include a touch screen display, and a user may interact with external device 16 via the display.

A user, such as a physician, technician, or other clinician, may interact with external device 16 to communicate with IMD 14. For example, the user may interact with external device 16 to retrieve physiological or diagnostic information from IMD 14. A user may also interact with external device 16 to program IMD 14, e.g., select values for operational parameters of monitor 14.

For example, the user may use external device 16 to retrieve information from IMD 14 regarding the rhythm of the heart of patient 12 (e.g., determined based on the signals from optical sensors 18, 20), trends of the heart rhythm over time or arrhythmia episodes. As another example, the user may use external device 16 to retrieve information from IMD 14 regarding other sensed physiological parameters of patient 12, such as blood oxygen saturation levels of patient 12. As another example, the user may use external device 16 to retrieve information from IMD 14 regarding the performance or integrity of IMD 14.

IMD 14 and external device 16 may communicate via wireless communication using any techniques known in the art. Examples of communication techniques may include, for example, low frequency or radiofrequency (RF) telemetry, but other techniques are also contemplated. In some examples, external device 16 may include a programming head that may be placed proximate to the patient's body near the implant site of IMD 14 in order to improve the quality or security of communication between IMD 14 and external device 16.

Figure 2:
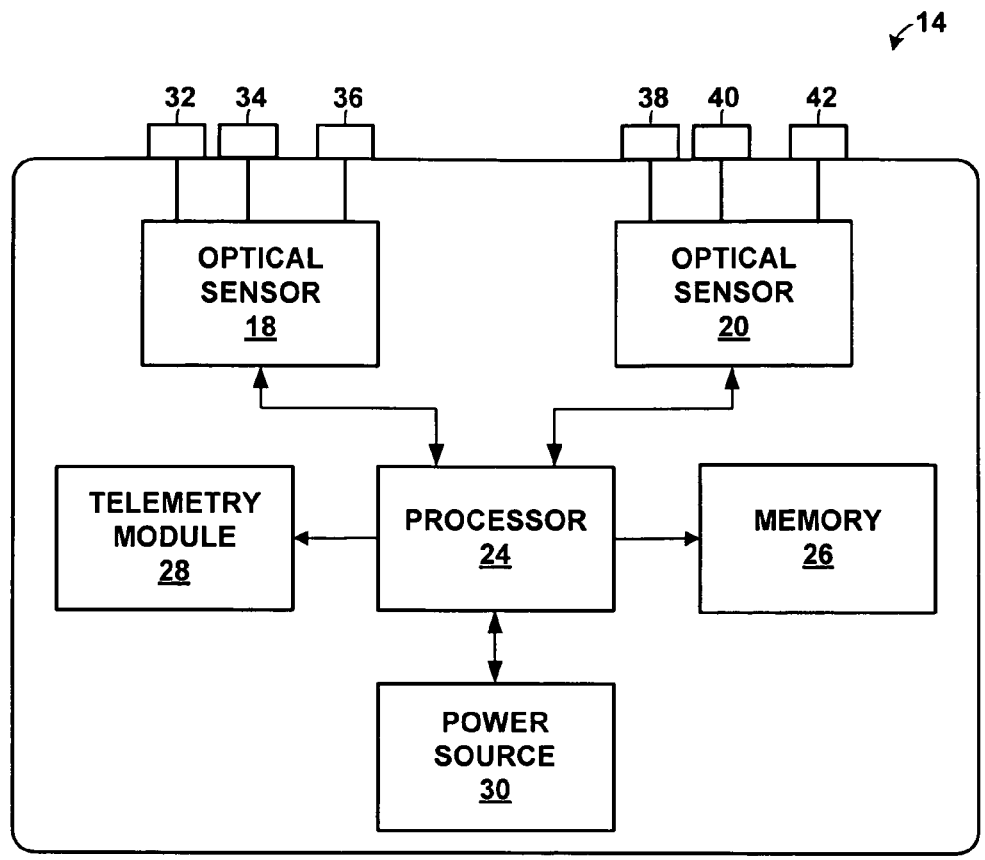
FIG. 2 is a functional block diagram of an example IMD that includes optical tissue sensors.

FIG. 2 is a block diagram of an example IMD 14. In the example shown in FIG. 2, IMD 14 includes optical sensors 18, 20, processor 24, memory 26, telemetry module 28, and power source 30. Memory 26 includes computer-readable instructions that, when executed by processor 24, cause IMD 14 and processor 24 to perform various functions attributed to IMD 14 and processor 24 herein. Memory 26 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 24 may include any one or more microprocessors, controllers, digital signal processors (DSPs), application specific integrated circuits (ASICs), field-programmable gate arrays (FPGAs), or equivalent discrete or integrated logic circuitry, or combinations thereof. In some examples, processor 24 may include multiple components, such as any combination of one or more microprocessors, one or more controllers, one or more DSPs, one or more ASICs, or one or more FPGAs, as well as other discrete or integrated logic circuitry. The functions attributed to processor 24 herein may be embodied as software, firmware, hardware or any combination thereof.

Processor 24 controls optical sensors 18, 20 to generate electrical signals indicative of the relative volume of oxygenated blood in tissue adjacent to optical sensors 18, 20. In the example shown in FIG. 2, optical sensor 18 includes red LED 32, IR LED 34, and detector 36, and optical sensor 20 includes red LED 38, IR LED 40, and detector 42. LEDs 32, 34, 38, 40 and detectors 36, 42 may be coupled to an outer surface of housing 22 of IMD 14 or may be disposed in recesses defined by housing 22 of IMD 14. Red LEDs 32, 38 may emit light in the red portion of the visible light spectrum, such, but not limited to, light having a wavelength in a range of about 550 nanometers (nm) to about 750 nm. IR LEDs 34, 40 may emit IR light in the IR portion of the light spectrum, such as, but not limited to, light having a wavelength in a range of about 750 nm to about 2.5 micrometers or greater. In other examples, optical sensors 18, 20 may comprise any suitable light source in addition to or instead to LEDs. For example, optical sensors 18, 20 may comprise a laser diode, a vertical cavity surface emitting laser device, a broadband light source, and the like.

Detector 36 of optical sensor 18 is configured to detect light emitted by red LED 32 and IR LED 34, and detector 42 of optical sensor 20 is configured to detect light emitted by red LED 38 and IR LED 40. Detectors 36, 42 may each include, for example, one or more photodetectors, such as photodiodes. For example, detectors 36, 42 may each include one photodiode sensitive to two or more wavelengths of light (e.g., light in the red spectrum and the IR spectrum) or multiple photodiodes that are each sensitive to a respective wavelength of light. Detectors 36, 42 are each configured to convert light incident on a photodetection surface of the respective detector 36, 42 into either a current or voltage, which may be outputted as an electrical signal. An intensity of the signal received by detectors 36, 42 may be indicative of hemodynamic function, such as the oxygen saturation of blood or the relative volume of blood in an artery of patient 12 by which IMD 14 is implanted. In examples in which detectors 36, 42 each include a photodiode, an electrical signal outputted by the detectors 36, 42 may be directly or inversely proportional to the amount of light (e.g., the intensity of light) incident on the photodiode.

Processor 24 may store electrical signals generated by detectors 36, 42 of optical sensors 18, 20 or values derived from the electrical signals generated by detectors 36, 42 in memory 26. Processor 24 may control the operation of LEDs 32, 34, 38, 40. In some examples, processor 24 may control red LED 32 and IR LED 34 of optical sensor 18 to sequentially emit light, such that only one of the LEDs 32, 34 emits light at a time. Similarly, in some examples, processor 24 may control red LED 38 and IR LED 40 to sequentially emit light, i.e., one after the other in respective time slots.

Processor 24 may also control the operation of detectors 36, 42. Light sensed by detector 36 of optical sensor 18 may include information about the intensity of red light emitted by red LED 32 and reflected by blood, as well as the intensity of IR light emitted by IR LED 34 and reflected by blood. In order to separate the signals indicative of the red light and IR light, processor 24 may demodulate the electrical signal received from detector 36. Similarly, in order to separate the signals indicative of the red light emitted by red LED 38 and reflected by blood and IR light emitted by IR LED 40 and reflected by blood, processor 24 may demodulate the electrical signal received from detector 42 of optical sensor 20. In some examples, processor 24 may oscillate the output of red LED 38 and IR LED 40 at different frequencies. For example, the current into red LED 38 may be driven at approximately 100 kilohertz (kHz) and the current into IR LED 40 may be driven at approximately 130 kHz. The signal from the single detector 36 may be electrically filtered to provide an output at 100 kHz and another at 130 kHz.

Optical sensors 18, 20 are fixed in positions relative to housing 22 (FIG. 1) of IMD 14, such that sensors 18, 20 are a predetermined distance apart upon implantation in patient 12. In some examples, sensor 18, 20 are about 0.5 millimeters (mm) to about 60 mm apart. In other examples, such as examples in which at least one of the optical sensors 18, 20 is disposed in a separate housing (e.g., implanted remotely from IMD 14) and wirelessly communicates with IMD 14, the distance between the remote optical sensor and the optical sensor or sensors in IMD 14 may be up to about 500 mm. In some examples, an optical barrier may be positioned between optical sensors 18, 20 in order to help prevent detector 36 of optical sensor 18 from sensing light emitted by red LED 38 and IR LED 40 of optical sensor 20, and to help prevent detector 42 of optical sensor 20 from sensing light emitted by LEDs 32, 34 of optical sensor 18. In addition, in some examples, an optical barrier may be positioned between detector 36 and LEDs 32, 34 of optical sensor 18 and between detector 42 and LEDs 38, 40 of optical sensor 20 to block direct transmission of light from LEDs 32, 34, 38, 40 to the respective detector 36, 42. In some examples, optical sensors 18, 20 may each include lenses that helps focus light emitted from the respective LEDs 32, 34, 38, 40.

IMD 14 may be subcutaneously or submuscularly implanted within patient 12 such that LEDs 32, 34, 38, 40 and detectors 36, 42 are oriented toward blood perfused tissue of patient 12, e.g., proximate to an artery of patient 12. In the example shown in FIG. 2, red LED 32 and IR LED 34 are positioned on the same side of the blood perfused tissue as detector 36, such that detector 36 detects light emitted by LEDs 32, 34 and reflected by the patient's blood. For example, red LED 32, IR LED 34, and detector 36 may be coupled to a common surface of housing 22 of IMD 14. Similarly, in the example shown in FIG. 2, red LED 38 and IR LED 40 are positioned on the same side of the blood perfused tissue as detector 42, such that detector 42 detects light emitted by LEDs 38, 40 and reflected by the patient's blood. In other examples, detectors 36, 42 may be positioned to detect light that is emitted by LEDs 32, 34, 38, 40 transmitted through the blood perfused tissue. This latter example is commonly referred to as a transmissive optical sensor.

Telemetry module 28 includes any suitable hardware, firmware, software or any combination thereof for communicating with another device, such as external device 16 (FIG. 1) or programmer 42 (FIG. 2). Under the control of processor 24, telemetry module 28 may receive downlink telemetry from and send uplink telemetry to external device with the aid of an antenna, which may be internal and/or external. Processor 24 may provide the data to be uplinked to external device 16 and the control signals for the telemetry circuit within telemetry module 28, e.g., via an address/data bus. In some examples, telemetry module 28 may provide received data to processor 24 via a multiplexer. In some examples, telemetry module 28 may wirelessly receive sensor signals from a remote optical sensor (not shown in FIG. 2) that is separated from the IMD 14.

The various components of IMD 14 are coupled to power source 30, which may include a rechargeable or non-rechargeable battery. A non-rechargeable battery may be selected to last for several years, while a rechargeable battery may be inductively charged from an external device, e.g., on a daily or weekly basis.

The block diagram shown in FIG. 2 is merely one example of an IMD 14. In other examples, IMD 14 may include a fewer number or a greater number of components. For example, in examples in which IMD 14 is incorporated with a medical device that delivers therapy to patient 12, IMD 14 may also include a therapy delivery module, such as an electrical stimulation generator or a fluid pump. For example, IMD 14 may include a therapy delivery module that delivers pacing, defibrillation or cardioversion pulses to a heart of patient 12, or may generate and deliver neurostimulation signals to a target tissue site within patient 12 (e.g., proximate to a spine or nerve, or to a target region of tissue that may or may not be near a nerve).

Although optical sensors 18, 20 are shown to be separate from processor 24 in FIG. 1, in other examples, processor 24 may include the functionality attributed to optical sensors 18, 20 herein and may be coupled to LEDs 32, 34, 38, 40 and detectors 36, 42. For example, optical sensors 18, 20 shown in FIG. 2 may include software executed by processor 24. If optical sensors 18, 20 include firmware or hardware, optical sensors 18, 20, respectively, may be a separate one of the one or more processors 24 or may be a part of a multifunction processor. As previously described, processor 24 may comprise one or more processors.

In some examples, some of the components of IMD 14 shown in the example of FIG. 2 may be located in another device. For example, although optical sensors 18, 20 are shown in FIG. 2 to be incorporated within housing 22 (FIG. 1) of IMD 14 that also encloses other components, such as processor 24 and memory 26, in other examples, optical sensors 18, 20 may be enclosed in separate housings, such that optical sensors 18, 20 may be separately implanted within patient 12.

Optical sensors 18, 20 that are enclosed in separate housings may include respective processors, telemetry modules, memories, and power sources, or one of the optical sensors may be a master sensor that controls the other optical sensor in a master-slave configuration. For example, optical sensor 18 may be a master module that provides power to optical sensor 20 and controls when red LED 38 and IR LED 40 emit light. In such examples, optical sensor 18 may communicate with optical sensor 20 via a wired connection or via wireless communication techniques, such as RF telemetry. Communication between separately housed optical sensors 18, 20 may be desirable in order to permit optical sensor 18 to, for example, receive an electrical signal generated by optical sensor 20 and stores the electrical signal in a memory enclosed in a common housing with optical sensor 18.

If optical sensors 18, 20 are enclosed in separate housings, the optical sensors 18, 20 may be mechanically coupled to each other or may be mechanically decoupled from each other. For example, optical sensors 18, 20 may be decoupled and implanted a predetermined distance from each other within patient 12. The clinician may generally implant optical sensors 18, 20 in patient 12 a predetermined distance apart. Although optical sensors 18, 20 may shift after implantation in patient 12, optical sensors 18, 20 may remain a generally known distance apart. In other examples in which optical sensors 18, 20 are enclosed in separate housings, the housings of optical sensors 18, 20 may be tethered together or otherwise coupled together with a flexible or a rigid coupling member. The coupling member may help fix a distance of separation between optical sensors 18, 20.

In some examples, data from at least one of the optical sensors 18, 20 may be uploaded to a remote server, from which a clinician or another user may access the data to analyze the patient's condition. An example of a remote server is a server provided via the Medtronic CareLink® Network, available from Medtronic, Inc. of Minneapolis, Minn.

Figure 3:
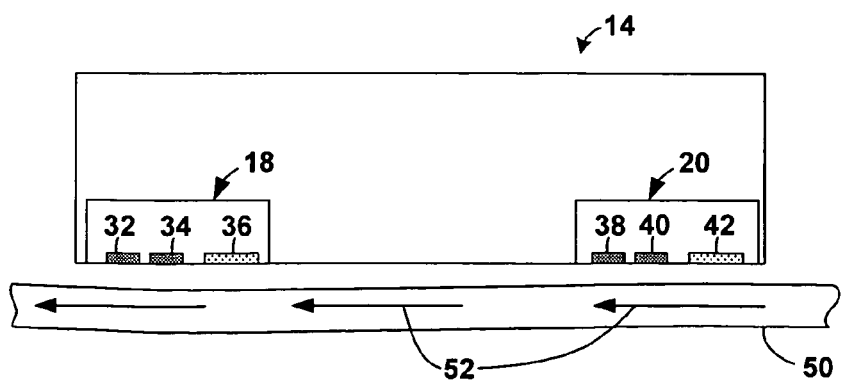
FIG. 3 is a conceptual illustration of an IMD including two optical sensors implanted proximate to an artery.

FIG. 3 is a conceptual illustration of IMD 14 implanted proximate to artery 50. Arrows 52 indicate a direction of blood flow through artery 50, which is generally a direction away from heart because artery 50 is typically a blood vessel that carries oxygenated blood away from the heart of patient 12. Accordingly, artery 50 may be referred to as a systemic artery. In the conceptual illustration shown in FIG. 3, IMD 14 is implanted proximate to artery 50 such that red LED 32 and IR LED 34 of optical sensor 18 emit light in a direction toward artery 50 and detector 36 senses light emitted by LEDs 32, 34 and reflected by blood within artery 50. In addition, IMD 14 is implanted such that red LED 38 and IR LED 40 of optical sensor 20 emit light in a direction toward artery 50 and detector 42 senses light emitted by LEDs 38, 40 and reflected by blood in artery 50.

IMD 14 is implanted within patient 12 such that optical sensor 18 is downstream of optical sensor 20 relative to a direction of blood flow within artery 50. In the example shown in FIG. 3, optical sensors 18, 20 generally face the same direction within patient 12 (e.g., do not face in opposite directions). For example, optical sensors 18, 20 may be positioned on a common surface of housing 22 of IMD 14. The planes of the photodetection surfaces of detectors 36, 42 may be, for example, substantially parallel.

Patient motion may cause optical sensors 18, 20 to provide a signal similar to that caused by arterial pressure pulses through artery 50 because the patient movement may cause relative movement between optical sensors 18, 20 and patient tissue, which may change the optical path between sensors 18, 20 and artery 50 or may change the amount of blood in artery 50, and, therefore, change the absorption of light by artery 50. Processor 24 (FIG. 2) may distinguish between pulses resulting from patient motion and pulses resulting from true heart activity with the aid of signals from both of the optical sensors 18, 20. In particular, processor 24 may implement various techniques based on the electrical signals from two optical sensors 18, 20 implanted within patient 12 such that optical sensor 18 is downstream of optical sensor 20 to minimize the effects of motion artifacts on the detection of arterial pulses from the electrical signals generated by optical sensors 18, 20. Example techniques are described in further detail with respect to FIGS. 5 and 7.

Due to their locations relative to each other and to the blood flow through artery 50, as indicated by arrows 52, optical sensor 20 may detect an arterial pulsation that results from a contraction of the patient's heart prior to the detection of the arterial pulsation by optical sensor 18. Optical sensors 18, 20 generally will not detect the arterial pulsation at the same time because the different implant sites of optical sensors 18, 20 relative to the direction 52 of blood flow through artery 50. Accordingly, a first electrical signal generated by optical sensor 20 and a second electrical signal generated by optical sensor 18 will not exhibit signal characteristics that indicate an arterial pulsation (e.g., a low amplitude) at substantially the same time. Rather, the one or more signal characteristics that indicate an arterial pulse will occur with a delay between the first and second electrical signals. The time delay may be a function of the distance between optical sensors 18, 20 (e.g., a distance between detectors 36, 42) and a speed of propagation of arterial pressure wave through an artery by which optical sensors 18, 20 are implanted. In this manner, based on the presence of delay, signal characteristics arising from arterial pulses may be distinguished from signal characteristics caused by motion. The velocity of the pressure pulse in an artery, such as a radial artery, may be about 6 meters per second (m/s) to about 15 m/s. Therefore, in some examples, the time delay between a signal characteristic that indicates an arterial pulse may be, for example, about 0.5 milliseconds (ms) to about 7 ms for optical sensors 18, 20 that are displaced by 7 and 40 mm along the artery, although other time delays are contemplated.

Figure 4:
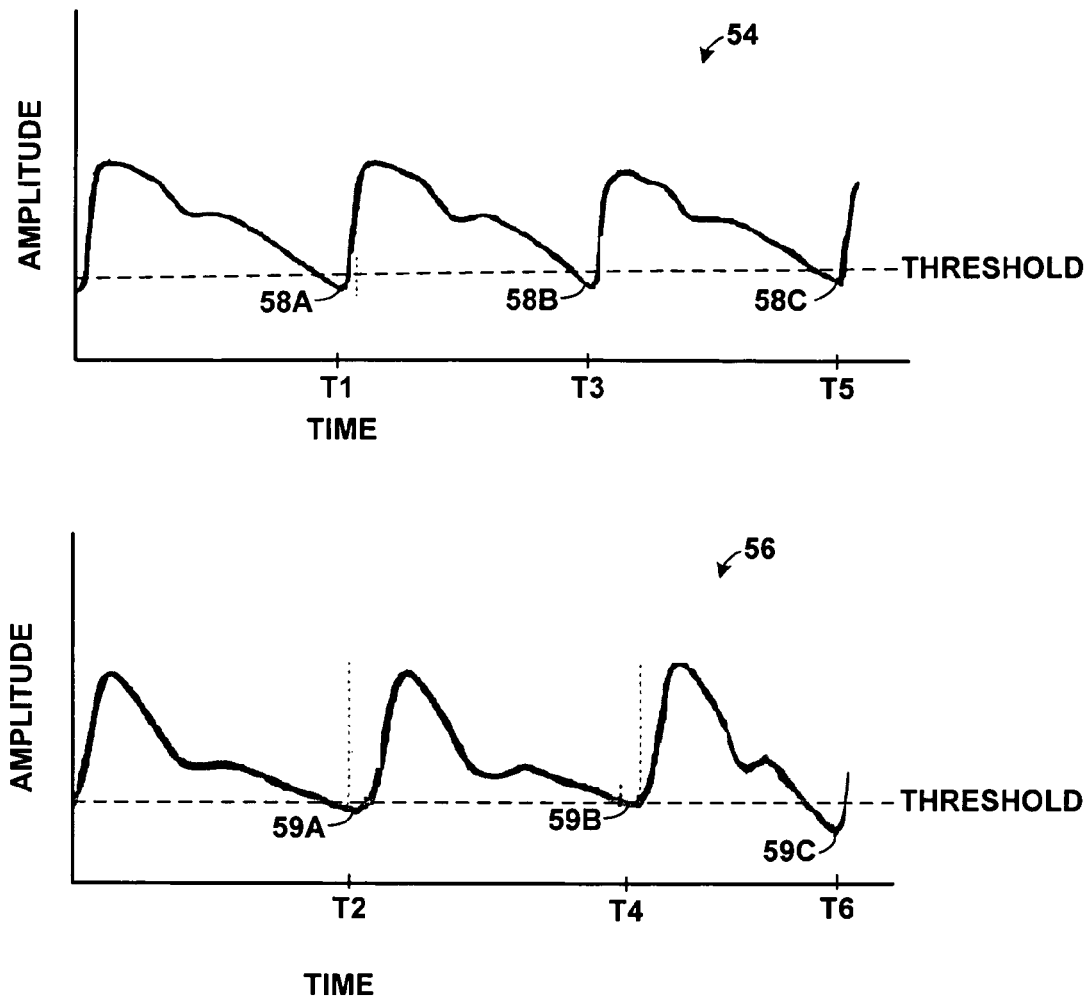
FIG. 4 illustrates example electrical signals generated by optical sensors.

FIG. 4 illustrates an example of electrical signals from optical sensors 18, 20. First electrical signal 54 is generated by detector 42 of optical sensor 20 and second electrical signal 56 is generated by detector 36 of optical sensor 18. Electrical signals 54, 56 change as a function of the amount of blood in tissue adjacent to optical sensors 18, 20. In the example shown in FIG. 3, for example, an amplitude of electrical signals 54, 56 may change as a function of blood in artery 50. The electrical signals 54, 56 shown in FIG. 4 are conceptual examples and are not intended to represent actual electrical signals generated by optical sensors.

As described with respect to FIG. 3, due to their locations relative to each other and to the direction of blood flow through artery 50, optical sensor 20 may detect an arterial pulse that results from a contraction of the patient's heart prior to the detection of the same arterial pulse by optical sensor 18. As described above with respect to FIG. 1, in some examples, an arterial pulsation may be represented by a trough amplitude value of the electrical signals 54, 56 because maximum light absorbance by the blood may occur during systole, which may be indicated by a low intensity of light incident on detectors 36, 42 of optical sensors 18, 20. The trough amplitude value may be determined to be an amplitude below a particular threshold (schematically shown in FIG. 4) or a lowest amplitude of the electrical signal within a particular range of time (e.g., determined based on the expected time interval between consecutive arterial pulses).

In the example shown in FIG. 4, electrical signal 54 generated by optical sensor 20 exhibits a trough 58A (i.e., a smallest relative amplitude within a certain time window) at time T1, which is associated with an arterial pulse resting from contraction of the patient's heart. Electrical signal 56 generated by optical sensor 18 exhibits a trough 59A at time T2, which is after time T1, which indicates the occurrence of the same arterial pulse. Because optical sensor 18 is positioned downstream of optical sensor 20, the delay indicated by the difference between times T1 and T2 may be attributable to the flow of blood through artery 50. That is, optical sensor 18 does not sense the increase in oxygenated blood volume until after optical sensor 20 senses the increase in oxygenated blood volume because the oxygenated blood flow reaches the portion of artery 50 proximate optical sensor 18 after the oxygenated blood flow reaches the portion of artery 50 proximate optical sensor 20.

In the example shown in FIG. 4, electrical signal 54 generated by optical sensor 20 exhibits a trough 58B at time T3, which is associated with an arterial pulse following the arterial pulse that was detected at time T1. Electrical signal 56 generated by optical sensor 18 exhibits a corresponding trough 59B at time T4, which is after time T3 and indicates the occurrence of the same arterial pulse indicated by electrical signal 54 at time T3.

Electrical signals 54, 56 generated by detectors 36, 42 of sensors 18, 20, respectively, may include motion artifacts from motion of patient 12. For example, motion artifacts may be introduced into signals 54, 56 by movement of the patient's muscle proximate to sensors 18, 20 or by motion of the sensor due to activities like walking or running. The motion of patient 12 may cause spurious pulses that are similar to pulses caused by arterial blood flow. Processor 24 may receive the spurious pulses and characterize the pulses as indicative of arterial blood flow, rather than motion, which may result in an erroneous and inaccurate reading of the patient's cardiac activity.

Although sensors 18, 20 are separated by a specific distance, motion of patient 12 may affect the output of detectors 36, 42 of sensors 18, 20, respectively, substantially similarly. In particular, electrical signals 54, 56 may exhibit signal characteristics that are attributable to motion artifacts at substantially the same time. For example, in FIG. 4, electrical signal 54 generated by detector 42 of optical sensor 20 exhibits a trough amplitude 58C at time T5, and processor 24 (FIG. 2) may determine that an arterial pulse was detected based on the detected trough amplitude at time T5. Electrical signal 56 generated by detector 36 of optical sensor 20 also exhibits a trough amplitude 59C at time T5.

Processor 24 may receive signals 54, 56 and determine that because both optical sensors 18, 20 generated an electrical signal indicative of an arterial pulse of patient 12 at time T5, the detected arterial pulse was a spurious pulse. Processor 24 may then disregard the arterial pulse detected at time T5. In this way, IMD 14 including two optical sensors 18, 20 implanted proximate to artery 50 and separated by a specific distance along the direction of blood flow through artery 50 may be used to minimize the impact of motion artifacts on the accuracy and precision of IMD 14 in detecting arterial pulses of patient 12. An example processing technique processor 24 may implement in order to determine when the electrical signals from optical sensors 18, 20 indicate a true arterial pulse, rather than motion artifacts, is described with respect to FIG. 7. IMD 14 including two optical sensors 18, 20 implanted proximate to artery 50 and separated by a specific distance along the direction of blood flow through artery 50 may allow increase in specificity of sensors 18, 20 to recognize true arterial pulses based on the delay in the signals generated by sensors 18, 20, and reject other signals that may be interpreted as arterial pulses if the delay were not used to filter them out.

Figure 5:
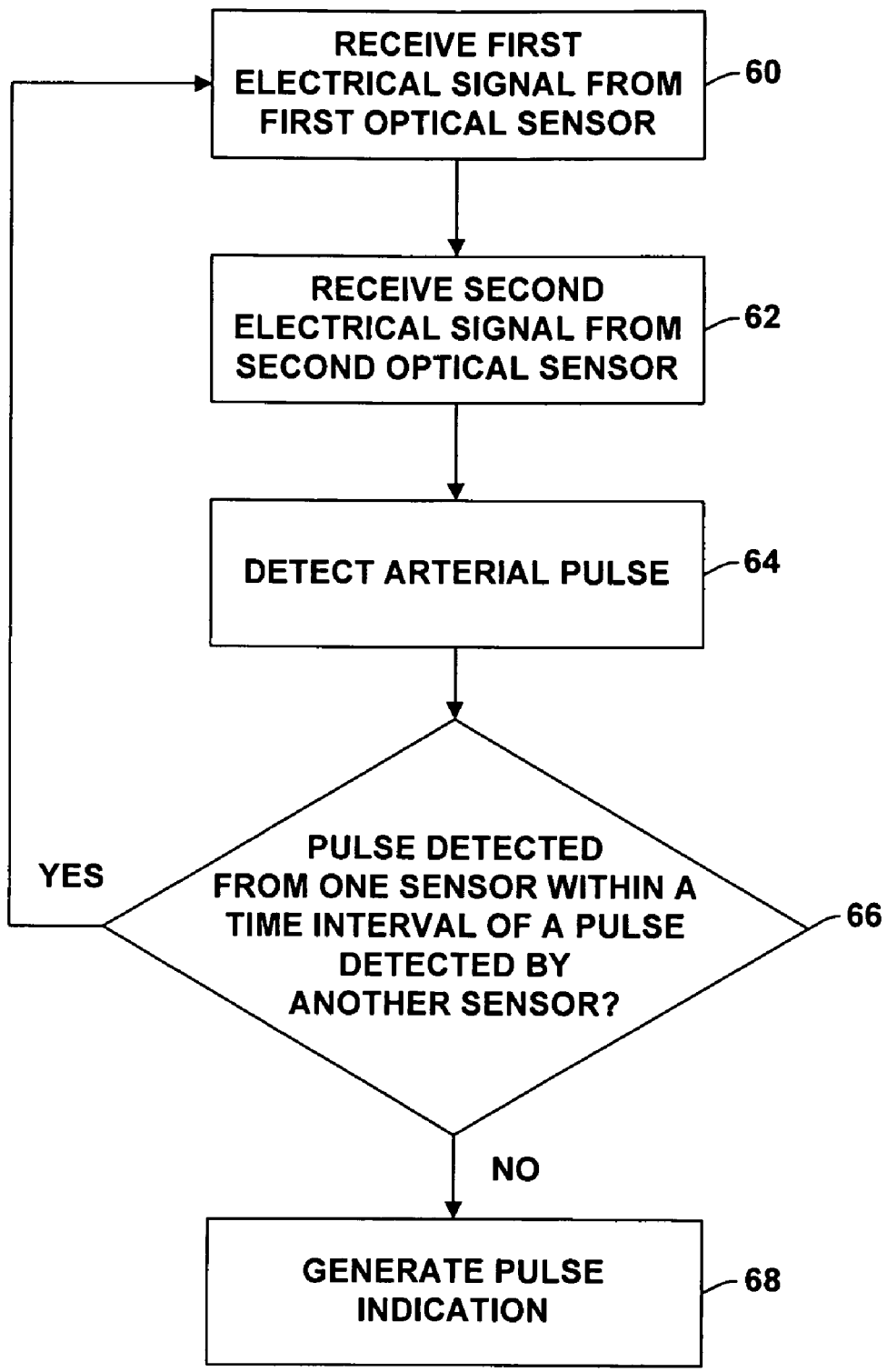
FIG. 5 is a flow diagram illustrating an example technique for determining whether an arterial pulse detected based on signals from one or more optical sensors is a spurious pulse or a true arterial pulse.

FIG. 5 is a flow diagram illustrating an example technique for detecting an arterial pulse from electrical signals provided by optical sensors 18, 20 implanted within patient 12 proximate to artery 50, where sensor 20 is implanted upstream of sensor 18 relative to the direction of blood flow through artery 50. The technique shown in FIG. 5 may be implemented by processor 24 of IMD 14 (FIG. 2) or a processor of another device, such as external device 16 (FIG. 1) in order to detect arterial pulses from electrical signals that may include motion artifacts. While processor 24 is referred to throughout the description of FIG. 5, as well as FIG. 7, in other examples, a processor of another device may implement the techniques shown in FIGS. 5 and 7.

Processor 24 may receive first electrical signal 54 (FIG. 4) from optical sensor 20 (60) and second electrical signal 56 (FIG. 4) from optical sensor 18 (62). Processor 24 may detect an arterial pulse based on at least one of the first signal 54 or the second signal 56 (64). As described above, in some examples, processor 24 may detect an arterial pulse when a trough amplitude of the first and/or second electrical signal waveforms is detected.

In other examples, processor 24 may detect an arterial pulse by normalizing a high pass filtered signal (e.g., with a high pass cutoff frequency of about 0.4 Hertz (Hz) and a low pass cutoff frequency of about 10 Hz) of a detected optical signal 54, 56 with a low pass filtered version (e.g., with a cutoff frequency of about 0.1 Hz) of the detected optical signal. Normalization will reduce signal amplitude variations due to changes in tissue attenuation and venous blood volume. If at least one of the LEDs of the respective sensor 18, 20 emits light having an oxygen insensitive wavelength (i.e., isobestic), such as about 805 nm, the respective signal 54, 56 generated by the sensor 18 or 20 may be oxygen insensitive and a resulting pulsatile waveform may have a normalized amplitude under various physiologic variations. In such examples, processor 24 may employ zero-crossing detection to detect an arterial pulse and the time delay between zero-crossings of signals 54, 56 generated by sensors 18, 20, respectively, may be compared to determine whether the zero-crossing of either signal 54, 56 indicates a true arterial pulse. In other examples, processor 24 may detect an arterial pulse based on optical signals 54, 56 when the respective optical signal crosses a threshold other than a zero-threshold.

In some examples, a fundamental frequency of the pulsatile waveform may be calculated based on the time of the zero-crossings to verify that the detected signal 54, 56 is physiologic signal. If the fundamental frequency of the pulsatile waveform is substantially similar to the expected frequency of a normal physiologic signal of patient 12, processor 24 may determine that the signals 54, 56 indicate a true arterial pulse, rather than motion artifacts. An expected frequency of a normal physiologic signal of patient 12 may be the frequency associated with a heart rate of patient 12, which may result in a pulsatile signal having a frequency of about 0.67 Hz to about 3 Hz (e.g., about 40 beats per minute to about 180 beats per minute).

A period of the pulsatile waveform for each of the signals 54, 56 may be determined to be the time period between zero-crossings, if the zero-crossings for only positive slopes are determined. If the zero-crossings for both positive and negative slopes are determined by processor 24, one period of the pulsatile waveform for each of the signals 54, 56 may be determined to be the time period between every other detected zero-crossing. The calculated frequency of the pulsatile waveform may be calculated based on the periods between zero-crossings (e.g., the frequency may be substantially equal to the inverse of the calculated period). The calculated frequency may be compared to the expected frequency of a physiologic signal of patient 12 (e.g., a heart rate of patient 12).

Processor 24 may analyze electrical signals 54, 56 and determine whether a signal characteristic indicating a pulse was detected from one sensor 18 or 20 within a time interval of detecting a signal characteristic indicating a pulse on another sensor 18 or 20 (66). The time interval may be, for example, within about 1 ms, such as less than about 0.5 ms, although other time intervals are contemplated. For example, processor 24 may determine whether the first and second electrical signals 54, 56 exhibited a trough amplitude value at substantially the same time or whether the signals 54, 56 exhibit a zero-crossing (or other threshold crossing) at substantially the same time.

If pulses were detected based on signal characteristics of the first and second electrical signals 54, 56 within a predetermined time range (or interval) of one another, processor 24 may reject pulse detection as being attributable to motion rather than a true arterial pulse. That is, processor 24 may determine that the detected pulse was a spurious pulse at least partially attributable to patient motion. Processor 24 may then continue monitoring the first electrical signal 54 (60) and the second electrical signal (62) until another arterial pulse (64) is detected.

If the first and second electrical signals 54, 56 did not indicate the occurrence of an arterial pulse within the predetermined range of time (66), processor 24 may determine that the detected arterial pulse is a true arterial pulse, and may generate a pulse indication (68). The pulse indication may be a value, flag, or signal that is stored or transmitted to indicate the occurrence of an arterial pulse, which may be indicative of systolic activity of the patient's heart. The pulse indication may be stored in memory 26 of IMD 14 or a memory of another device, such as external device 16 (FIG. 1). The stored pulse indications may be used to determine the patient's cardiac activity, e.g., the patient's heart rate, which may be used to assess the patient's cardiac health.

Figure 6:
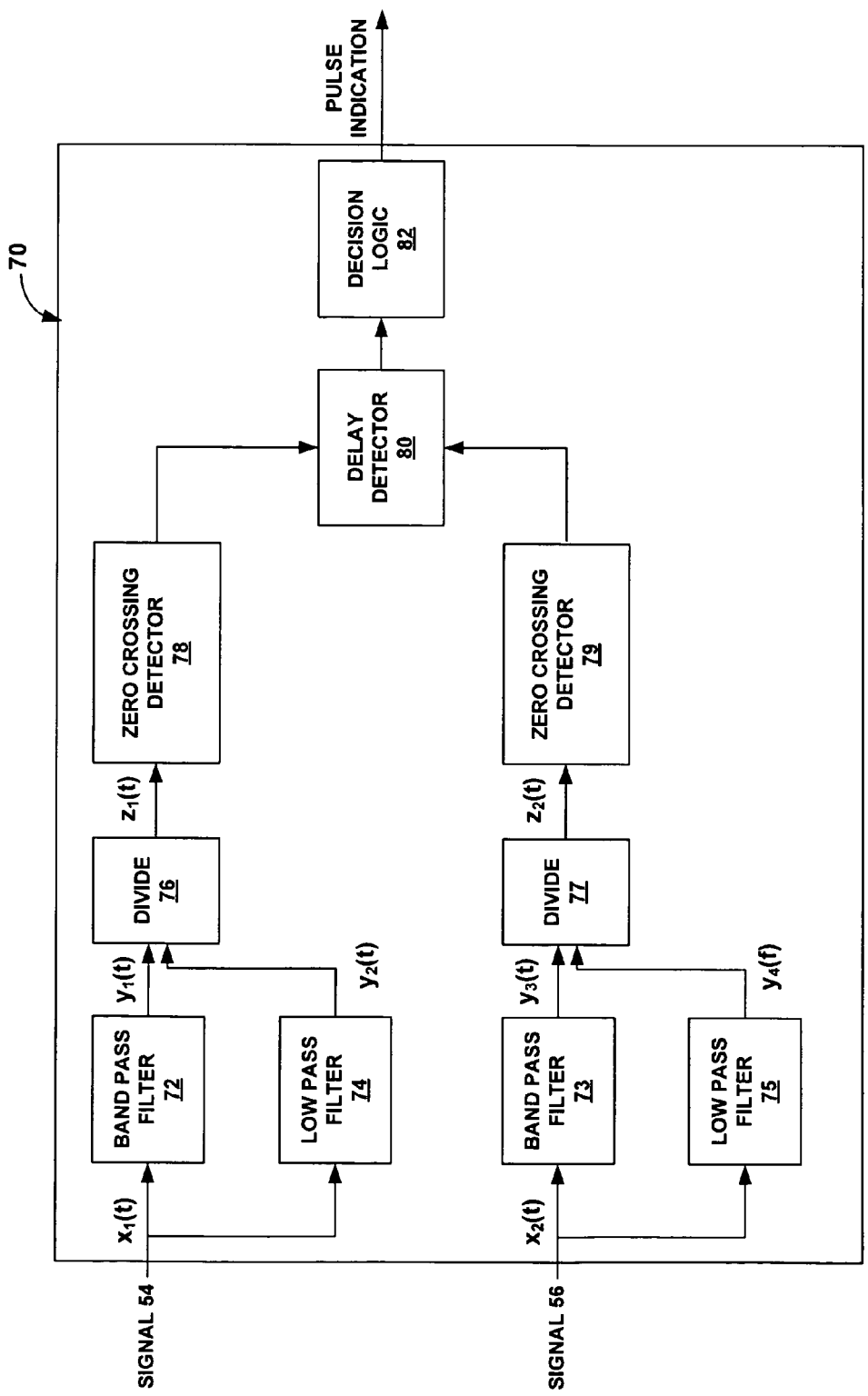
FIG. 6 is a logic diagram illustrating an example circuit that generates a pulse indication based on electrical signals generated by two optical sensors.

FIG. 6 is a logic diagram illustrating an example circuit of module 70 that may detect a pulse from optical signals 54, 56 generated by optical sensors 18, 20, respectively, and generate a pulse indication if the pulse is determined to be a true arterial pulse. Module 70 may be integrated into processor 24 of IMD 14 (FIG. 2) or of another device, such as external device 16 (FIG. 1). Electrical signal 54 (FIG. 4) generated by optical sensor 20 may be transmitted into module 70 and provided to band pass filter 72 and low pass filter 74. Electrical signal 56 (FIG. 4) generated by optical sensor 18 may be transmitted into module 70 and provided to band pass filter 73 and low pass filter 75. Although not shown in FIG. 6, in some examples, electrical signal 54, 56 may be provided to an amplifier prior to being sent to the respective band pass filters 72, 73 and low pass filters 74, 75.

In some examples, electrical signal 54, 56 may include a pulsatile waveform (or component) and one or more other components. The pulsatile waveform may be modulated by the arterial pulses sensed by optical sensor 18, 20. That is, the waveforms of the electrical signals 54, 56 generated by optical sensors 18, 20 may change in response to the increased blood volume in artery 50 resulting from the arterial pulses. The other waveforms that may be present in electrical signals 54, 56 may be generated by various causes. For example, optical sensors 18, 20 may detect blood within through tissue surrounding artery 50, i.e. tissue perfusion. The blood in the tissue may cause volume changes that are detected by optical sensors 18, 20.

Tissue perfusion may be detected by optical sensors 18, 20 and included in the generated signals 54, 56 along with the measurements of the arterial pulse resulting in an electrical signal that includes the waveform for an arterial pulse and one or more other waveforms. The volume of blood within tissue (i.e., tissue perfusion) may not change as fast as the volume of blood within artery 50 that results from arterial pulses. As a result, the pulsatile waveform that results from arterial pulses may have a frequency that is greater than the frequency of the one or more other waveforms, e.g., waveforms indicating changes in tissue perfusion. In some examples, the amplitude of the pulsatile waveform may be less than the amplitude of the one or more other waveforms, e.g., waveforms indicating tissue perfusion. Accordingly, it may be necessary to normalize the amplitude of the pulsatile waveform to minimize the effects of detected changes in blood volume that are attributable to tissue perfusion on the amplitude of the pulsatile component of signals 54, 56. Normalizing the electrical signals 54, 56 may provide a better measurement of a detected arterial pulse and better generation of a pulse indication based on electrical signals generated by optical sensors 18, 20.

As shown in FIG. 6, electrical signal 54 may be represented as $x_1(t)$, and electrical signal 56 may be represented as $x_2(t)$. Electrical signal 54 is filtered by band pass filter 72 and low pass filter 74. Similarly, electrical signal 56 is filtered by band pass filter 73 and low pass filter 75. Band pass filters 72, 73 may generally have the same cutoff frequencies, and low pass filters 74, 75 may have the same cutoff frequencies. In other examples, band pass filters 72, 73 may have different cutoff frequencies and/or low pass filters 74, 75 may have different cutoff frequencies. In some examples, the high pass cutoff frequency of band pass filters 72, 73 may be approximately 0.4 Hz and the low pass cutoff frequency of band pass filters 72, 73 may be approximately 10 Hz. In other examples, the low pass cutoff frequency of band pass filters 72, 73 may be approximately 40 Hz. In some examples, the low pass cutoff frequency of low pass filters 74, 75 may be approximately 0.1 Hz.

Band pass filters 72, 73 may remove the direct current (DC) voltage component of electrical signal 54, 56, respectively. After electrical signal 54, 56 are filtered by band pass filter 72, 73, the signals outputted by band pass filter 72, 73 toggle around approximately zero volts, i.e., the peak of filtered signals 54, 56 may be greater than approximately zero volts and the trough of filtered signals 54, 56 may be less than zero volts.

Band pass filter 72, 73 may filter electrical signal 54, 56, respectively, to reduce the amplitude of waveforms that are not the pulsatile waveform, i.e., are not attributable to the pulses (e.g., arterial pulses or pulses attributable to motion artifacts) sensed by optical sensors 18, 20, and limit the frequency range of the pulsatile waveform. Low pass filter 74, 75 may also filter electrical signal 54, 56, respectively, to reduce the amplitude of the waveforms that are not part of the pulsatile waveform component. Because low pass filters 74, 75 may have a lower cutoff frequency compared to band pass filters 72, 73, the combination of low pass filters 74, 75 and band pass filters 72, 73, respectively, may reduce the amplitude of waveforms other than the pulsatile waveform component better than either the band pass filters 72, 73 alone or the low pass filters 74, 75 alone. In this manner, the pulsatile waveform of signals 54, 56 may be the dominant waveform of the filtered signals because the amplitudes of the extraneous waveforms are reduced by the passing of electrical signals 54, 56 through the filters 72-75.

Although band pass filters 72, 73 and low pass filters 74, 75 reduce the amplitude of the extraneous waveforms of electrical signals 54, 56, i.e. waveforms that are not the pulsatile waveform, the amplitude of the peak and trough of the remaining waveform may vary due to nonpulsatile waveforms that may not be filtered out by filters 72-75. Accordingly, it may be necessary to normalize the amplitude of the filtered signals 54, 56 to minimize the varying peak and trough amplitudes.

Signal $y_1(t)$ results after electrical signal 54 is filtered by band pass filter 74, and signal $y_2(t)$ results after electrical signal 54 is filtered by low pass filter 74. Similarly, $y_3(t)$ results after electrical signal 56 is filtered by band pass filter 73 and $y_4(t)$ results after electrical signal 56 is filtered by low pass filter 75. Signals $y_1(t)$ and $y_3(t)$ toggle across approximately zero volts because their respective DC components are substantially removed by band pass filters 72, 73, respectively. Signals $y_1(t)$ and $y_2(t)$ are outputted to divide module 76 that divides signal $y_1(t)$ by signal $y_2(t)$ to generate a signal that normalizes the amplitude of the pulsatile waveform component of electrical signal 54, shown as $z_1(t)$ in FIG. 6. Similarly, signal $y_3(t)$ and $y_4(t)$ are outputted to divide module 77 that divides signal $y_3(t)$ by signal $y_4(t)$ to generate a signal $z_2(t)$ having a normalized amplitude.

Signals $z_1(t)$ and $z_2(t)$ are outputted to zero crossing detectors 78, 79, respectively. Zero crossing detectors 78, 79 determine when the voltage level of signal $z_1(t)$, $z_2(t)$, respectively, cross 0 volts. For example, zero crossing detector 78 may output a pulse when the voltage of signal $z_1(t)$ changes from a negative value to a positive value and/or changes from a positive value to a negative value. Zero crossing detector 79 may also output a pulse when the voltage of signal $z_1(t)$ changes from a negative value to a positive value and/or changes from a positive value to a negative value. In some examples, zero crossing detectors 78, 79 may each comprise a Schmitt trigger.

Though not shown in FIG. 6, in some examples, module 70 may include two slope detectors, whereby one slope detector is coupled to the output of divider module 76, and the other slope detector coupled to the output of divider module 77. In such examples, zero crossing detectors 78, 79 may receive signal $z_1(t)$ and $z_2(t)$, respectively, as well as the output of the respective slope detectors. The slope detectors may determine when signals $z_1(t)$ and $z_2(t)$ are on either rising edges or falling edge. For example, if the slope of signal $z_1(t)$ is positive, signal $z_1(t)$ is on a rising edge, similarly, if the slope of signal $z_1(t)$ is negative, signal $z_1(t)$ is on a falling edge. As described above, zero crossing detectors 78, 79 may output a pulse whenever signals $z_1(t)$ and $z_2(t)$, respectively, cross zero volts. In examples that include slope detectors, zero crossing detector 78, 79 may only output a pulse whenever signals $z_1(t)$ and $z_2(t)$, respectively, cross zero volts on a rising edge, and do not output a pulse whenever signals $z_1(t)$ and $z_2(t)$ cross zero volts on a falling edge. Alternatively, zero crossing detector 78, 79 may only output a pulse whenever signals $z_1(t)$ and $z_2(t)$, respectively, cross zero volts on a falling edge, and do not output a pulse whenever signals $z_1(t)$ and $z_2(t)$ cross zero volts on a rising edge.

Generally, zero crossing detector 78, 79, such as Schmitt triggers, may be sensitive to fluctuations in voltages that cross zero volts. In many instances, noise or other factors may cause signal $z_1(t)$ and $z_2(t)$ to inadvertently fluctuate around zero volts. For example, even though the amplitude of extraneous waveforms, described above, have been reduced, and the amplitude of the pulsatile waveform has been normalized, the extraneous waveforms may still add some fluctuation to the pulsatile waveform, which may cause signals $z_1(t)$ and $z_2(t)$ to inadvertently cross zero volts. Zero crossing detector 78, 79 may recognize this and output a pulse in response.

To address this inadvertent pulse output from zero crossing detector 78, 79, in some embodiments, zero crossing detectors 78, 79 may each include hysteresis. Hysteresis provides a dual threshold action such that a first input level results in an output, and the output stays in that state until the input changes to a second input level that is different than the first input level. For example, if signal $z_1(t)$ has an amplitude of approximately 1 volt such that signal $z_1(t)$ toggles from approximately 0.5 volts to approximately −0.5 volts across 0 volts, zero crossing detector 78 may include a hysteresis threshold at 0.1 volts and −0.1 volts. In this example, on a rising edge, zero crossing detector 78 may not recognize that signal $z_1(t)$ has crossed zero volts until signal $z_1(t)$ crosses 0.1 volts. Then, on a falling edge, zero crossing detector 78 may not recognize that signal $z_1(t)$ has crossed zero volts until signal $z_1(t)$ crosses −0.1 volts. In this manner, any voltage fluctuations between −0.1 volts and 0.1 volts are discarded by zero crossing detector 78 and not considered to be a zero-crossing.

Zero crossing detector 79 may be substantially similar to zero crossing detector 78. In examples in which module 70 includes slope detectors for both zero crossing detectors 78, 79, and zero crossing detectors 78, 79 output a pulse only on rising edges of signal $z_1(t)$ and $z_2(t)$, respectively, zero crossing detectors 78, 79 may only output a pulse when signal $z_1(t)$ crosses a particular threshold, such as 0.1 volts. Similarly, in examples in which zero crossing detectors 78, 79 output a pulse only on falling edges of signal $z_1(t)$ and $z_2(t)$, zero crossing detectors 78, 79 may only output a pulse when signals $z_1(t)$ and $z_2(t)$, respectively, cross a particular threshold, such as −0.1 volts.

The output of zero crossing detector 78 and 79 are outputted to delay detector 80. The zero crossings of signals $z_1(t)$ and $z_2(t)$ may indicate the frequency of the pulsatile waveform of electrical signals 54, 56, respectively, generated by optical sensors 18, 20, respectively. In order to ensure that delay detector 80 compares the time interval between relevant zero crossings of signals $z_1(t)$ and $z_2(t)$, e.g., zero crossings that indicate the occurrence of the same pulse or the same motion artifact, zero crossing detector 78 may employ the slope detector. In this way, delay detector 80 may only compare the time interval between respective rising edge zero crossings of signals $z_1(t)$ and $z_2(t)$ or respective falling edges of signals $z_1(t)$ and $z_2(t)$.

For example, in examples in which zero crossing detectors 78, 79 only detect either the rising edge zero crossings or falling edge zero crossings, each zero crossing of signals $z_1(t)$ and $z_2(t)$ may indicate a pulse detected by optical sensors 18, 20. Delay detector 80 may compare the zero crossings detected by zero crossing detectors 78, 79 to determine the delay between the pulses detected by sensors 18, 20. Decision logic 82 may determine that if signals 54, 56 (or signals $z_1(t)$ and $z_2(t)$) exhibited a zero crossing at substantially the same time or within a particular time range, such as within 0.5 milliseconds of each other, the detected pulse associated with the zero crossings was not indicate a true arterial pulse. On the other hand, if delay detector 80 indicates that electrical signal 54 exhibited a zero crossing before electrical signal 56, e.g., within about 0.5 milliseconds to about 7 milliseconds of each other, decision logic 82 may determine that the zero crossings of the signals 54, 56 (or signals $z_1(t)$ and $z_2(t)$) indicates the detected pulse associated with the zero crossings was a true arterial pulse. Decision logic 82 may then generate a pulse indication.

In examples in which zero crossing detectors 78, 79 detect both the rising edge zero crossings and the falling edge zero crossings, every two zero crossings of signals $z_1(t)$ and $z_2(t)$ may indicate each pulse detected by optical sensors 18, 20. In such examples, delay detector 80 may compare time intervals between every two zero crossings detected by zero crossing detectors 78, 79 to determine the delay between the detected pulses.

Figure 7:
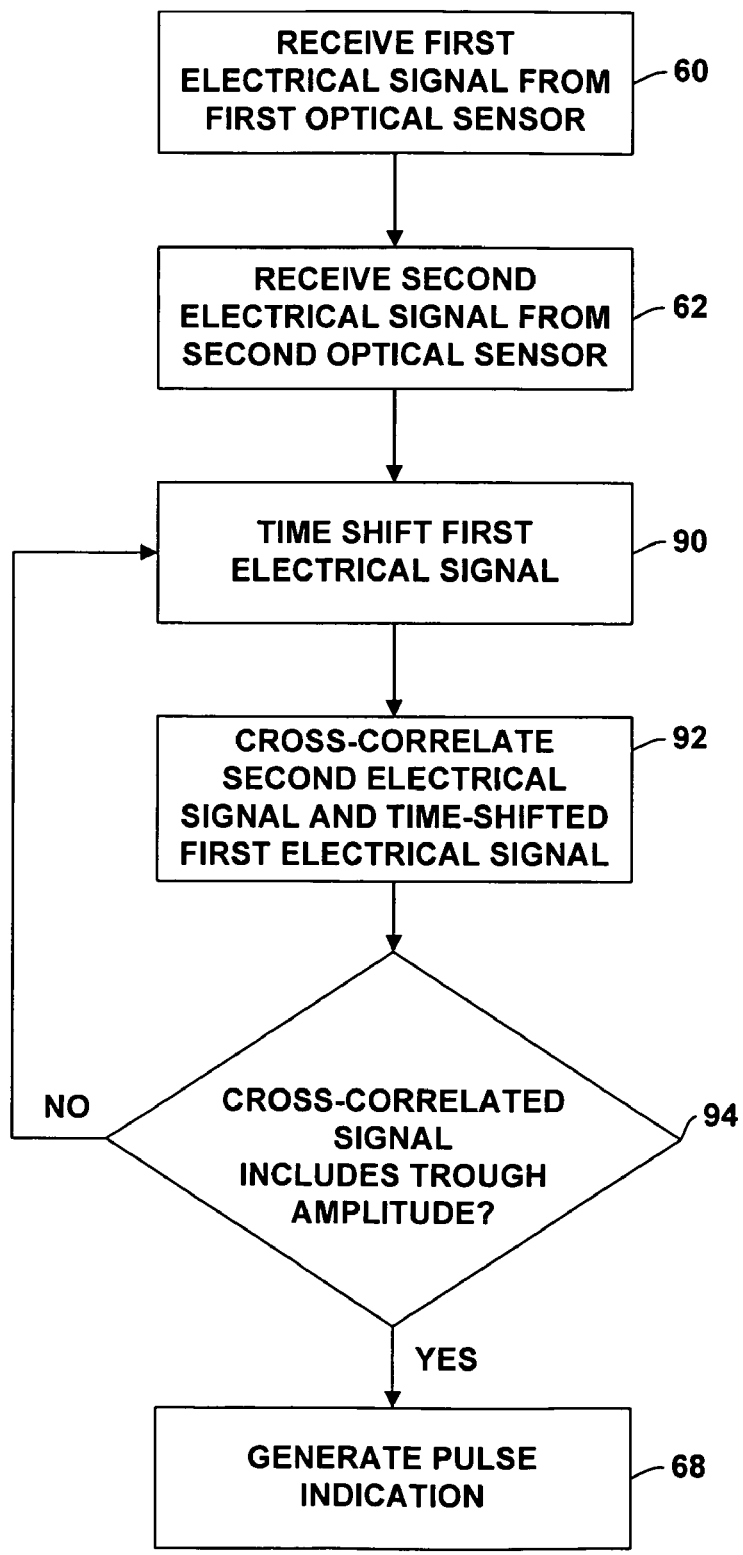
FIG. 7 is a flow diagram illustrating an example technique for detecting an arterial pulse from electrical signals provided by two optical sensors implanted within a patient proximate to an artery and separated from each other by a specific distance.

FIG. 7 is a flow diagram illustrating a technique for detecting an arterial pulse detected based first electrical signal 54 and second electrical signal 56 (FIG. 4), which may help minimize the effects of motion artifacts on the detection of the arterial pulse. As with the technique shown in FIG. 5, processor 24 of IMD 14 may receive first electrical signal 54 from optical sensor 20 (60) and second electrical signal 56 from optical sensor 18 (62). As previously indicated, first electrical signal 54 generated by optical sensor 20 may indicate the occurrence of an arterial pulse before second electrical signal 56 generated by optical sensor 18 indicates the occurrence of the same arterial pulse. The delay in the detection of the arterial pulse based on the first and second electrical signals 54, 56 may be at least partially due to the orientation that IMD 14 is implanted within patient 12. In particular, IMD 14 is implanted within patient 12 such that optical sensor 20 is separated from optical sensor 18 and located along artery 50 upstream of optical sensor 18. The flow of blood through artery 50 may be sensed by optical sensor 20 prior to optical sensor 18. Thus, the flow of oxygenated blood through artery 50 that is associated with an arterial pulse may be sensed by optical sensor 20 before optical sensor 18.

In order to detect an arterial pulse, processor 24 may perform a signal processing operation that compares the two signals 54, 56 for non-randomness. In one example, processor 24 may cross-correlate first electrical signal 54 with second electrical signal 56. Cross-correlation is a signal processing technique in which first electrical signal 54 may be time shifted relative to second electrical signal 56 (90) and the two signals may be multiplied point by point. If an arterial pulse is present, a strong cross-correlation appears at time shifts that correspond to the expected time delay between the detection of an arterial pulse by optical sensors 18, 20. The amount of time that processor 24 shifts first electrical signal 54 relative to second electrical signal 56 may be, for example, less than or equal to the expected time delay between the detection of an arterial pulse by optical sensors 18, 20. The expected time delay may be, for example, determined based on the distance separating optical sensors 18, 20 (e.g., the distance separating detectors 36, 42) and the speed of propagation of blood through artery 50 following a contraction of the patient's heart (i.e., following a systole). It may also be measured using optical sensors 18, 20 during times when patient 12 is relatively motionless. In some examples, processor 24 may time shift first electrical signal 54 about 0.5 ms to about 80 ms relative to second electrical signal 56 (90).

Processor 24 may detect an arterial pulse at the time at which the correlated signal resulting from the signal processing of the second electrical signal 56 and the time shifted first electrical signal 54 exhibits a trough amplitude. In other examples, depending on the wavelength of light emitted by the light sources of sensors 18, 20, processor 24 may detect an arterial pulse at the time at which the correlated signal resulting from the signal processing of the second electrical signal 56 and the time shifted first electrical signal exhibits a peak amplitude.

Processor 24 may continue time shifting first electrical signal 54 (90) and cross-correlating second electrical signal 56 and the time-shifted first electrical signal 54 (92) until the cross-correlated electrical signal (e.g., the multiplied second electrical signal 56 and time-shifted first electrical signal 54) includes the trough amplitude value (94) or until a certain maximum amount of time for shifting first electrical signal 54 is reached. The maximum amount of time that first electrical signal 54 may be shifted to detect a trough amplitude value of the summed signals may be based on, for example, the expected delay between arterial pulse detection by first and second optical sensors 18, 20. The expected time delay may be, for example, 0.5 ms to about 7 ms. Accordingly, in some examples, the maximum amount of time that first electrical signal 54 may be shifted to detect a trough amplitude value of the summed signals may be equal to about 0.5 ms to about 7 ms. After detecting the trough amplitude value of the summed signal (94), processor 24 may generate a pulse indication (68). The pulse indication may indicate the detection of an arterial pulse as well as the time at which the pulse was detected.

In other examples of the technique shown in FIG. 7, processor 24 may time shift second electrical signal 56 rather than first electrical signal 54. Processor 24 may then correlate the first electrical signal 54 with the time-shifted second electrical signal 56 until a nadir point (or trough amplitude) is detected, indicating the occurrence of an arterial pulse, or until the maximum amount of time that second electrical signal 56 may be shifted is reached.

Although two techniques for determining whether first electrical signal 54 and second electrical signal 56 indicate the presence of an arterial pulse have been described herein with respect to FIGS. 5 and 7, processor 24 may implement other algorithms for detecting arterial pulses from first and/or second electrical signals 54, 56 and excluding spurious pulses attributable to motion artifacts.

Figure 8:
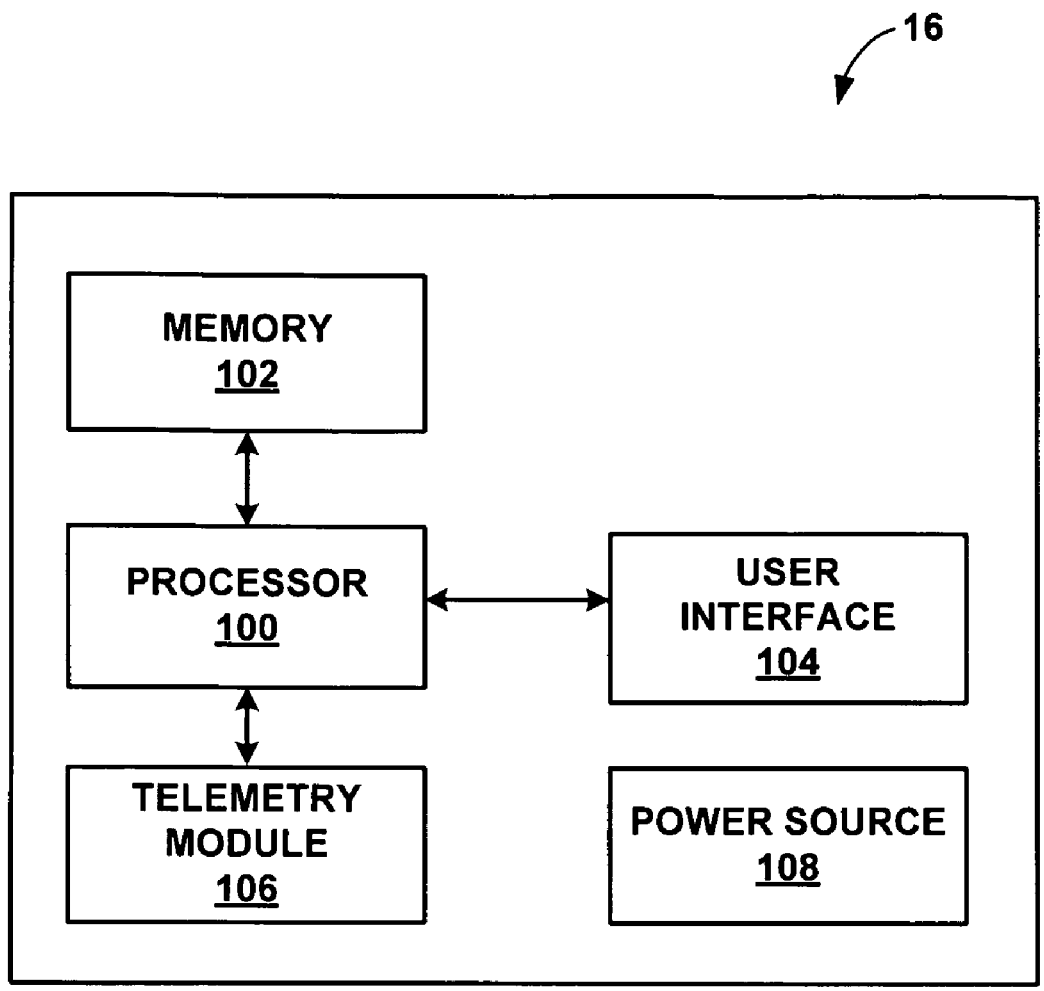
FIG. 8 is a functional block diagram of an example medical device programmer.

FIG. 8 is a block diagram of an example external device 16. As shown in FIG. 8, external device 16 includes processor 100, memory 102, user interface 104, telemetry module 106, and power source 108. External device 16 may be a dedicated hardware device with dedicated software for interrogating IMD 14 to obtain information stored in memory 26 (FIG. 2), and, in some examples, for programming IMD 14. Alternatively, external device 16 may be an off-the-shelf computing device running an application that enables external device 16 to communicate with IMD 14.

A user may use external device 16 to modify operating parameters of optical sensors 18, 20. For example, the user may program the frequency at which LEDs 32, 34, 38, 40 (FIG. 2) emit light and the frequency at which detectors 36, 42 provide processor 24 with electrical signals indicative of the blood flow through artery 50. The clinician may interact with external device 16 via user interface 104, which may include display to present graphical user interface to a user, and a keypad or another mechanism for receiving input from a user.

Processor 100 can take the form one or more microprocessors, DSPs, ASICs, FPGAs, programmable logic circuitry, or the like, and the functions attributed to processor 100 herein may be embodied as hardware, firmware, software or any combination thereof. Memory 102 may store instructions that cause processor 100 to provide the functionality ascribed to external device 16 herein, and information used by processor 100 to provide the functionality ascribed to external device 16 herein. Memory 102 may include any fixed or removable magnetic, optical, or electrical media, such as RAM, ROM, CD-ROM, hard or floppy magnetic disks, EEPROM, flash memory, or the like. Memory 102 may also include a removable memory portion that may be used to provide memory updates or increases in memory capacities. A removable memory may also allow patient data to be easily transferred to another computing device, or to be removed before external device 16 is used to program therapy for another patient.

External device 16 may communicate wirelessly with IMD 14, e.g., using RF communication or proximal inductive interaction. This wireless communication is possible through the use of telemetry module 106, which may be coupled to an internal antenna or an external antenna. An external antenna that is coupled to external device 16 may correspond to the programming head that may be placed over the implant site of IMD 14. Telemetry module 106 may be similar to telemetry module 28 of IMD 14 (FIG. 2).

Telemetry module 106 may also be configured to communicate with another computing device via wireless communication techniques, or direct communication through a wired connection. Examples of local wireless communication techniques that may be employed to facilitate communication between external device 16 and another computing device include RF communication according to the 802.11 or Bluetooth specification sets, infrared communication, e.g., according to the IrDA standard, or other standard or proprietary telemetry protocols. In this manner, other external devices may be capable of communicating with external device 16 without needing to establish a secure wireless connection.

Power source 108 delivers operating power to the components of external device 16. Power source 108 may include a battery and a power generation circuit to produce the operating power. In some examples, the battery may be rechargeable to allow extended operation. Recharging may be accomplished by electrically coupling power source 108 to a cradle or plug that is connected to an alternating current (AC) outlet. In addition or alternatively, recharging may be accomplished through proximal inductive interaction between an external charger and an inductive charging coil within external device 16.

In other examples, traditional batteries (e.g., nickel cadmium or lithium ion batteries) may be used. In addition, external device 16 may be directly coupled to an alternating current outlet to power external device 16. Power source 108 may include circuitry to monitor power remaining within a battery. In this manner, user interface 104 may provide a current battery level indicator or low battery level indicator when the battery needs to be replaced or recharged. In some cases, power source 108 may be capable of estimating the remaining time of operation using the current battery.

Figure 9A:
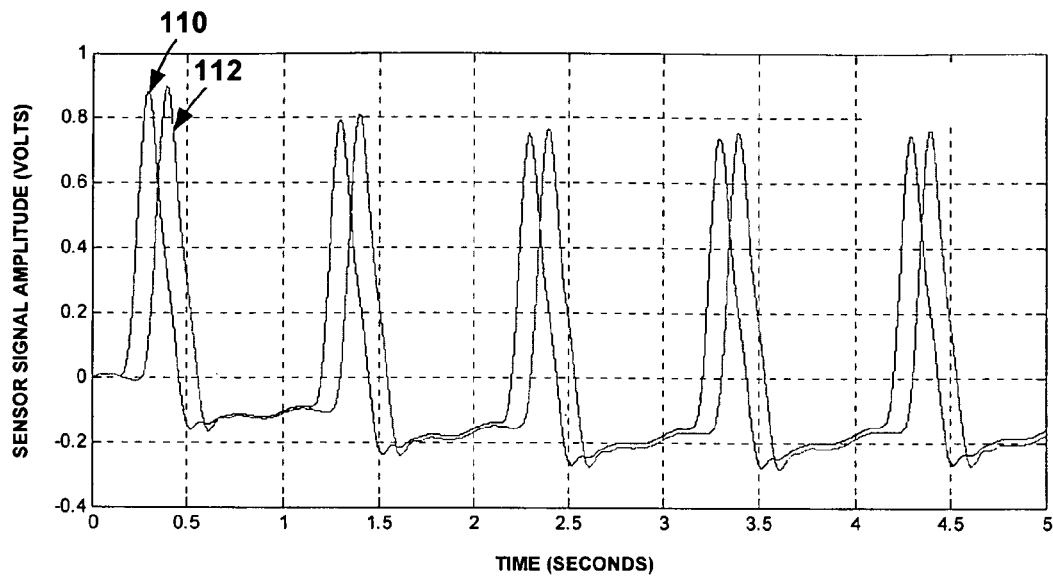
FIG. 9A is a conceptual illustration of electrical signals generated by optical sensors.

FIGS. 9A-10B illustrate different examples of how cross-correlating electrical signals from optical sensors 18, 20 that are implanted within patient 12 such that optical sensor 20 detects a true arterial pulse before optical sensor 20 may be used to reject motion artifacts. FIG. 9A illustrates electrical signal 110 generated by optical sensor 20 and electrical signal 112 generated by optical sensor 18 that is implanted downstream of optical sensor 20 in a direction of blood flow within artery 50. The frequency of each of the optical signals 110, 112 is about 1 Hz, and the peak-to-peak amplitude is about 1 Volt. The approximate time delay between the arterial pulses detected by optical signals 110, 112 is about 100 ms. In the example shown in FIG. 9A, a motion artifact signal present in optical signals 110, 112 has a frequency of about 3 Hz and a peak-to-peak amplitude of about 0.02 Volts.

Figure 9B:
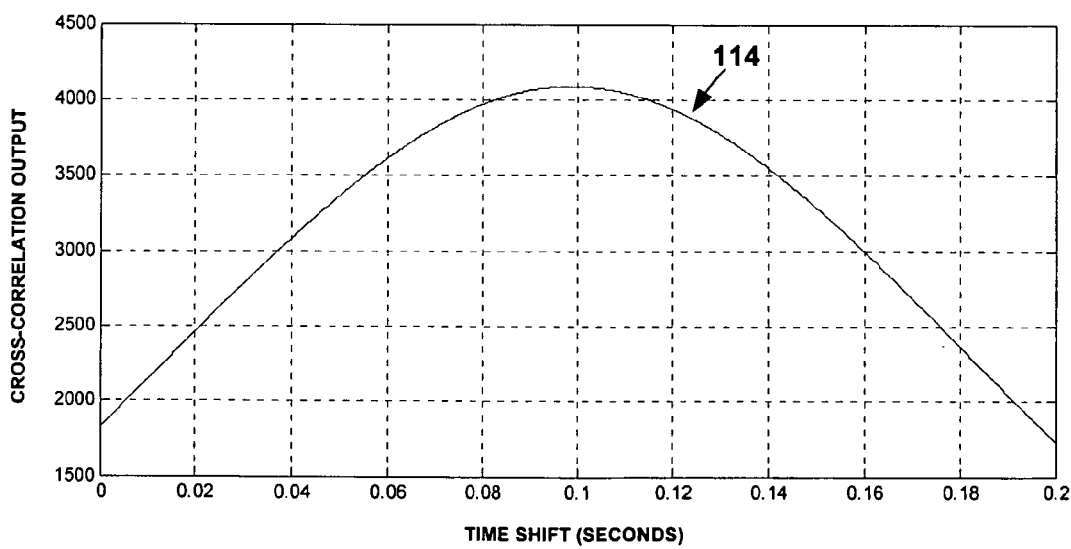
FIG. 9B is a conceptual illustration of a cross-correlated electrical signal generated based on the electrical signals shown in FIG. 9A.

FIG. 9B illustrates a cross-correlated signal 114 that may result when signal 110 is time shifted relative to signal 112 and the time-shifted signal 110 and signal 112 are multiplied. As FIG. 9B illustrates, cross-correlated signal 114 exhibits a peak amplitude when signal 110 is shifted about 0.1 seconds relative to signal 112. The cross-correlated signal 114 indicates that first and second signals 110, 112 indicate a true arterial pulse, with a time delay of about 0.1 seconds between the pulse detection based on first signal 110 and the pulse detection based on second signal 112.

Figure 10A:
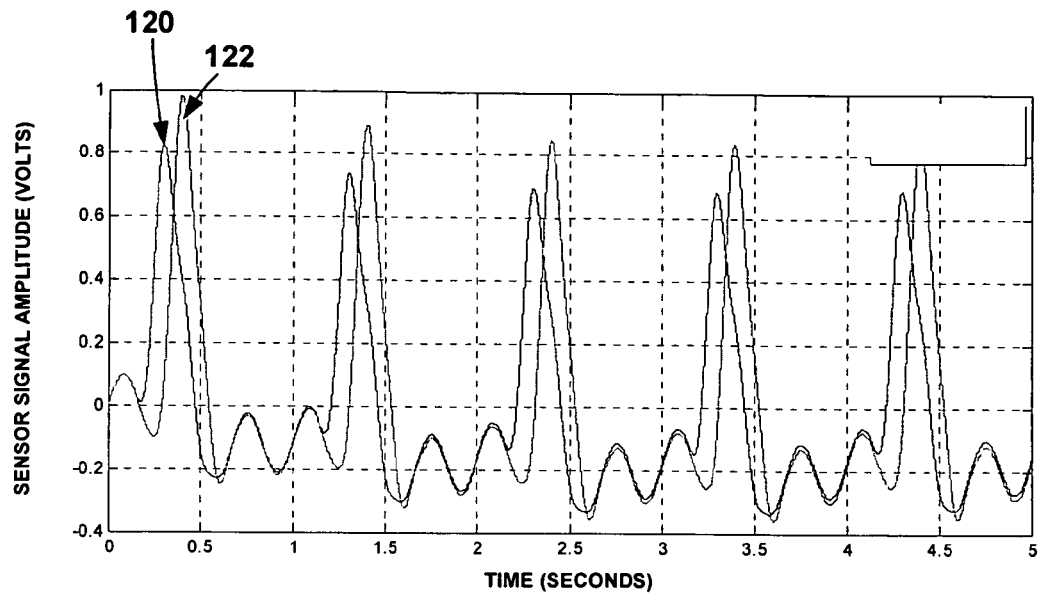
FIG. 10A is a conceptual illustration of electrical signals generated by optical sensors.
Figure 10B:
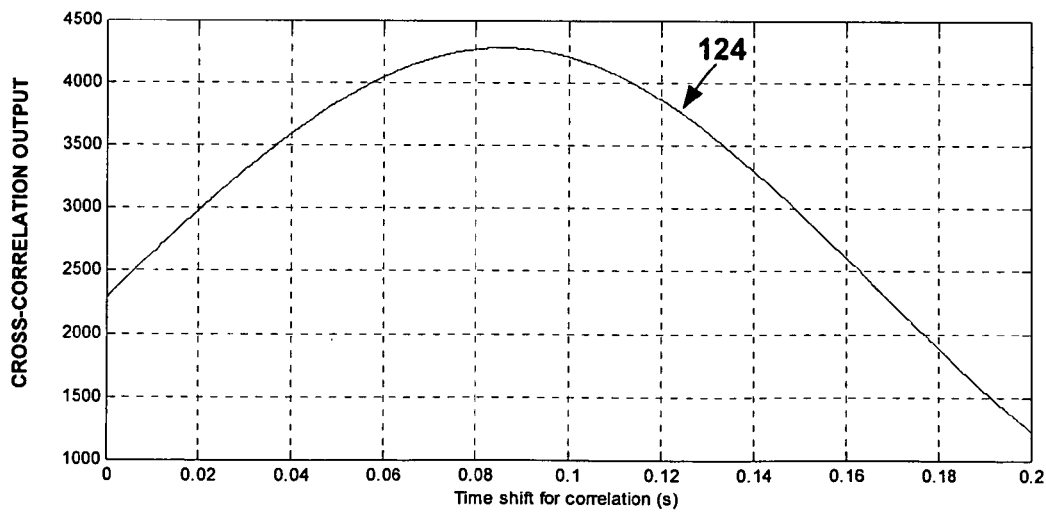
FIG. 10B is a conceptual illustration of a cross-correlated electrical signal generated based on the electrical signals shown in FIG. 10A.

FIGS. 10A and 10B illustrate another example of a cross-correlation of electrical signals generated by optical sensors 18, 20. FIG. 10A illustrates electrical signal 120 generated by optical sensor 20 and electrical signal 122 generated by optical sensor 18. The frequency of each of the optical signals 120, 122 is about 1 Hz, and the peak-to-peak amplitude is about 1 Volt. The approximate time delay between the arterial pulses detected by optical signals 120, 122 is about 100 ms. In the example shown in FIG. 10A, a motion artifact signal present in optical signals 120, 122 has a frequency of about 3 Hz and a peak-to-peak amplitude of about 0.2 Volts.

FIG. 10B illustrates a cross-correlated signal 124 that may result when signal 120 is time shifted relative to signal 122 and the time-shifted signal 120 and signal 122 are multiplied. As FIG. 10B illustrates, cross-correlated signal 124 exhibits a peak amplitude when signal 110 is shifted between about 0.08 seconds and 0.09 seconds relative to signal 112. The cross-correlated signal 124 indicates that first and second signals 120, 122 indicate a true arterial pulse, with a time delay of about 0.08-0.09 seconds between the pulse detection based on first signal 120 and the pulse detection based on second signal 122.

The techniques described in this disclosure, including those attributed to IMD 14, programmer 24, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

In other examples, the techniques described as being performed by processor 24 of IMD 14 may be performed in whole or in part by processor 100 of external device 16 or another device. For example, processor 100 of external device 16 may receive signals from optical sensors 18, 20 and determine whether a true arterial pulse has occurred based on the signals from optical sensors 18, 20. That is, processor 100 or another device external to patient 12 or implanted within patient 12 may use the signals from optical sensors 18, 20 that are implanted proximate to an artery and along the direction of blood flow in the artery to detect arterial pulses and determine whether a detected pulse is a true arterial pulse or a spurious pulse based on the delay between the signals generated by optical sensors 18, 20.

Various examples of medical systems and techniques have been described. These and other examples are within the scope of the following claims.

The invention claimed is:

1. A method comprising:
receiving, with a processor, a first electrical signal from a first optical sensor implanted within a patient;
receiving, with the processor, a second electrical signal from a second optical sensor implanted within the patient;
detecting, with the processor, an arterial pulse of the patient based on a first signal characteristic of the first electrical signal;
detecting, with the processor, a second signal characteristic of the second electrical signal indicative of the arterial pulse; and
determining, with the processor, whether the detected arterial pulse is a spurious pulse based on a time delay between the first and second signal characteristics.

2. The method of claim 1, wherein the first and second optical sensors are implanted along an artery of the patient.

3. The method of claim 2, wherein the second optical sensor is located downstream of the first optical sensor relative to a direction of blood flow in the artery.

4. The method of claim 1, wherein the first and second optical sensors are implanted along different arteries of the patient.

5. The method of claim 1, wherein the first and second optical sensors are coupled to a common housing.

6. The method of claim 5, wherein the housing defines a surface and the first and second optical sensors are coupled to the surface of the common housing.

7. The method of claim 1, wherein the first and second optical sensors comprise separate housings that are movable relative to each other.

8. The method of claim 1, wherein determining whether the detected arterial pulse is a spurious pulse comprises determining whether the first and second signal characteristics occurred within a predetermined range of time of one another, and if the first and second characteristics occurred within the predetermined range of time, determining that the detected arterial pulse is the spurious pulse.

9. The method of claim 8, wherein the predetermined range of time comprises less than about 0.5 milliseconds.

10. The method of claim 1, wherein the first and second signal characteristics comprise at least one of a peak amplitude, a trough amplitude or a threshold crossing.

11. The method of claim 1, wherein the first and second signal characteristics comprise threshold crossings of the first and second signals, respectively, and wherein detecting the arterial pulse comprises:
normalizing the first electrical signal; and
detecting a first threshold crossing of the normalized first electrical signal, wherein the first threshold crossing indicates the arterial pulse; and
wherein detecting the second signal characteristic of the second electrical signal indicative of the arterial pulse comprises:
normalizing the second electrical signal;
detecting a second threshold crossing of the normalized second electrical signal, wherein the second threshold crossing indicates the arterial pulse.

12. The method of claim 11, wherein determining whether the arterial pulse is a spurious pulse comprises determining whether the first and second threshold crossings occurred within a predetermined range of time of one another and if the first and second threshold crossings occurred within the predetermined range of time, determining that the detected arterial pulse is the spurious pulse.

13. The method of claim 12, wherein the predetermined range of time comprises less than about 0.5 milliseconds.

14. The method of claim 11, wherein the first and second thresholds each comprise approximately zero volts.

15. The method of claim 1, wherein the first electrical signal changes as a function of at least one of a blood oxygen saturation level of the patient and a blood volume of tissue of the patient proximate the first optical sensor, and wherein the second electrical signal changes as a function of at least one of the blood oxygen saturation level of the patient and a blood volume of tissue of the patient proximate the second optical sensor.

16. The method of claim 1, wherein determining whether the detected arterial pulse is a spurious pulse based on the time delay between the first and second signal characteristics comprises determining whether the first and second signal characteristics occurred at the same time, and determining that the detected arterial pulse is the spurious pulse in response to determining the first and second characteristics occurred at the same time.

17. The method of claim 1, wherein determining whether the detected arterial pulse is a spurious pulse based on the time delay between the first and second signal characteristics comprises determining whether the time delay between the first and second characteristics is within a predetermined range of values and determining that the detected arterial pulse is not the spurious pulse in response to determining the time delay is within the predetermined range of values.

18. The method of claim 17, wherein the predetermined range of values is about 0.5 milliseconds to about 7 milliseconds.

19. An implantable medical system comprising:
a first optical sensor configured to generate a first electrical signal;
a second optical sensor configured to generate a second electrical signal; and
a processor configured to receive the first electrical signal and the second electrical signal, detect an arterial pulse of the patient based on a first signal characteristic of the first electrical signal, detect a second signal characteristic of the second electrical signal indicative of the arterial pulse, and determine whether the detected arterial pulse is a spurious pulse based on a time delay between the first and second signal characteristics.

20. The implantable medical system of claim 19, wherein the first and second optical sensors each comprise at least one light source and at least one detector.

21. The implantable medical system of claim 19, wherein the first and second optical sensors are configured to be implanted along one or more arteries of the patient.

22. The implantable medical system of claim 19, wherein the first and second optical sensors are separated by a distance of about 0.5 millimeters to about 60 millimeters.

23. The implantable medical system of claim 19, wherein the second optical sensor is configured to be implanted downstream of the first optical sensor relative to a direction of blood flow in an artery of the patient.

24. The implantable medical system of claim 19, further comprising a housing, wherein the first and second optical sensors are coupled to the housing.

25. The implantable medical system of claim 19, wherein the first and second optical sensors comprise separate housings that are movable relative to each other.

26. The implantable medical system of claim 25, wherein the first and second optical sensors further comprise respective telemetry modules, and wherein the first and second optical sensors wirelessly communicate via the respective telemetry modules.

27. The implantable medical system of claim 19, wherein the processor is configured to determine whether the detected arterial pulse is a spurious pulse by at least determining whether the first and second signal characteristics occurred within a predetermined range of time, and wherein the processor is configured to determine that the detected arterial pulse is the spurious pulse if the first and second characteristics occurred within the predetermined range of time.

28. The implantable medical system of claim 27, wherein the predetermined range of time comprises less than about 0.5 milliseconds.

29. The implantable medical system of claim 19, wherein the first and second signal characteristics comprise at least one of a peak amplitude, a trough amplitude or a threshold crossing.

30. The implantable medical system of claim 19, wherein the first and second signal characteristics comprise threshold crossings of the first and second electrical signals, respectively, and wherein the processor is configured to detect the arterial pulse by at least normalizing the first electrical signal, and detecting a first threshold crossing of the normalized first electrical signal, wherein the first threshold crossing indicates the arterial pulse, and wherein the processor is configured to detect the second signal characteristic of the second electrical signal by at least normalizing the second electrical signal and detecting a second threshold crossing of the normalized second electrical signal, where the second threshold crossing indicates the arterial pulse.

31. The implantable medical system of claim 30, wherein the processor is configured to determine whether the arterial pulse is a spurious pulse by at least determining whether the first and second threshold crossings occurred within a predetermined range of time of one another and if the first and second threshold crossings occurred within the predetermined range of time, determining that the detected arterial pulse is the spurious pulse.

32. The implantable medical system claim 31, wherein the first and second thresholds each comprise approximately zero volts.

33. The implantable medical system of claim 19, wherein the first optical sensor is configured to generate the first electrical signal that changes as a function of at least one of a blood oxygen saturation level of the patient and a blood volume of tissue of the patient proximate the first optical sensor, and wherein the second optical sensor is configured to generate the second electrical signal that changes as a function of at least one of the blood oxygen saturation level of the patient and a blood volume of tissue of the patient proximate the second optical sensor.

34. The implantable medical system of claim 19, wherein the processor is configured to determine whether the detected arterial pulse is a spurious pulse based on the time delay between the first and second signal characteristics by at least determining whether the first and second signal characteristics occurred at the same time, and determining that the detected arterial pulse is the spurious pulse in response to determining the first and second characteristics occurred at the same time.

35. The implantable medical system of claim 19, wherein the processor is configured to determine whether the detected arterial pulse is a spurious pulse based on the time delay between the first and second signal characteristics by at least determining whether the time delay between the first and second characteristics is within a predetermined range of values and determining that the detected arterial pulse is not the spurious pulse in response to determining the time delay is within the predetermined range of values.

36. The implantable medical system of claim 35, wherein the predetermined range of values is about 0.5 milliseconds to about 7 milliseconds.

37. A medical system comprising:
means for receiving a first electrical signal from a first optical sensor implanted within a patient;
means for receiving a second electrical signal from a second optical sensor implanted within the patient;

means for detecting an arterial pulse of the patient based on at least one of the first or second electrical signals a first signal characteristic of the first electrical signal;

means for detecting a second signal characteristic of the second electrical signal indicative of the arterial pulse; and means for determining whether the detected arterial pulse is a spurious pulse based on a time delay between the first and second signal characteristics.

38. The medical system of claim 37, wherein the means for determining whether the detected arterial pulse is a spurious pulse comprises means for determining whether the first and second signal characteristics occurred within a predetermined range of time of one another, and if the first and second characteristics occurred within the predetermined range of time, the means for determining whether the detected arterial pulse is a spurious pulse determines that the detected arterial pulse is the spurious pulse.

39. The medical system of claim 37, wherein the first and second signal characteristics comprise threshold crossings of the first and second electrical signals, respectively, and wherein the means for detecting the arterial pulse comprises:
means for normalizing the first electrical signal;
means for detecting a first threshold crossing of the normalized first electrical signal, wherein the first threshold crossing indicates the arterial pulse; and
wherein the means for detecting the second signal characteristic comprises:
means for normalizing the second electrical signal; and
means for detecting a second threshold crossing of the normalized second electrical signal, wherein the second threshold crossing indicates the arterial pulse.

40. The medical system of claim 37, wherein the means for determining whether the detected arterial pulse is a spurious pulse based on the time delay between the first and second signal characteristics determines whether the first and second signal characteristics occurred at the same time, and determines that the detected arterial pulse is the spurious pulse in response to determining the first and second characteristics occurred at the same time.

41. The medical system of claim 37, wherein the means for determining whether the detected arterial pulse is a spurious pulse based on the time delay between the first and second signal characteristics determines whether the time delay between the first and second characteristics is within a predetermined range of values and determines that the detected arterial pulse is not the spurious pulse in response to determining the time delay is within the predetermined range of values.

42. A method comprising:
receiving a first electrical signal from a first optical sensor implanted within a patient;
receiving a second electrical signal from a second optical sensor implanted within the patient, wherein the first and second optical sensors are positioned relative to each other such that the first optical sensor detects an arterial pulse of the patient before the second optical sensor;
detecting a first signal characteristic of the first signal;
detecting a second signal characteristic of the second signal;
determining whether the first and second signal characteristics occurred within a predetermined range of time; and
if the first and second signal characteristics occurred within the predetermined range of time, determining that the first and second signal characteristics are artifacts.

43. The method of claim 42, wherein the first and second signal characteristics each comprise one of a peak amplitude, a trough amplitude or a threshold crossing.

* * * * *

UNITED STATES PATENT AND TRADEMARK OFFICE
CERTIFICATE OF CORRECTION

PATENT NO. : 8,273,032 B2
APPLICATION NO. : 12/182847
DATED : September 25, 2012
INVENTOR(S) : James Kevin Carney et al.

Page 1 of 1

It is certified that error appears in the above-identified patent and that said Letters Patent is hereby corrected as shown below:

Col. 26, line 29, delete "...system claim 31..." and insert in place thereof -- system of claim 31 --

Col. 27, line 2, delete "...based on at least one of the first or second electrical signals a first..." and insert in place thereof -- based on a first --

Signed and Sealed this
Fourth Day of December, 2012

David J. Kappos
*Director of the United States Patent and Trademark Office*